(12) United States Patent
Tomlinson

(10) Patent No.: US 10,406,016 B1
(45) Date of Patent: Sep. 10, 2019

(54) SPLINT KIT SET

(71) Applicant: Robert J. Tomlinson, Springdale, AR (US)

(72) Inventor: Robert J. Tomlinson, Springdale, AR (US)

(73) Assignee: READYSPLINTS L.L.C., Springdale, AR (US)

( * ) Notice: Subject to any disclaimer, the term of this patent is extended or adjusted under 35 U.S.C. 154(b) by 0 days.

(21) Appl. No.: 15/083,962

(22) Filed: Mar. 29, 2016

Related U.S. Application Data

(63) Continuation-in-part of application No. 14/447,252, filed on Jul. 30, 2014, now Pat. No. 10,143,584.

(51) Int. Cl.
*A61F 5/00* (2006.01)
*A61F 5/058* (2006.01)

(52) U.S. Cl.
CPC ...... *A61F 5/05841* (2013.01); *A61F 5/05825* (2013.01)

(58) Field of Classification Search
CPC ........ A61F 5/01; A61F 5/058; A61F 5/05866; A61F 5/05841; A61F 5/05875; A61F 2250/0062
USPC ...................................... 602/57, 59; D9/707
See application file for complete search history.

(56) References Cited

U.S. PATENT DOCUMENTS

| | | | | |
|---|---|---|---|---|
| 4,793,330 A | * | 12/1988 | Honeycutt | A61F 13/04 523/105 |
| 5,284,468 A | * | 2/1994 | Nelson | A61F 5/05825 602/5 |
| 5,480,376 A | * | 1/1996 | Duback | A41D 13/015 428/68 |
| 8,771,209 B2 | * | 7/2014 | Evans | A61F 13/00072 206/440 |
| 2006/0177162 A1 | * | 8/2006 | Harano | B65D 75/5816 383/202 |
| 2007/0122067 A1 | * | 5/2007 | Redmond | B65D 75/5822 383/200 |
| 2008/0023352 A1 | * | 1/2008 | Creed | B65D 73/0078 206/232 |
| 2011/0288463 A1 | * | 11/2011 | Girasa | A61F 15/002 602/57 |

* cited by examiner

*Primary Examiner* — Kim M Lewis
(74) *Attorney, Agent, or Firm* — Schrantz Law Firm, PLLC; Stephen D. Schrantz

(57) ABSTRACT

The splint kit provides a sealed splint, bandaging, and a water source for setting the splint. Different kits may be needed depending upon the size of the user to which the splint will be applied. The kits may also vary according to the body part to be set. The size of each splint is based upon the size of the user and the size of the body part(s) to be splinted to eliminate the need for the user to size the splint. The splint is self-contained in its own packaging to maintain the integrity of the splint. The fiberglass/hardening material is encased by a foam material and/or felt to further simplify the process of applying and setting the splint.

5 Claims, 41 Drawing Sheets

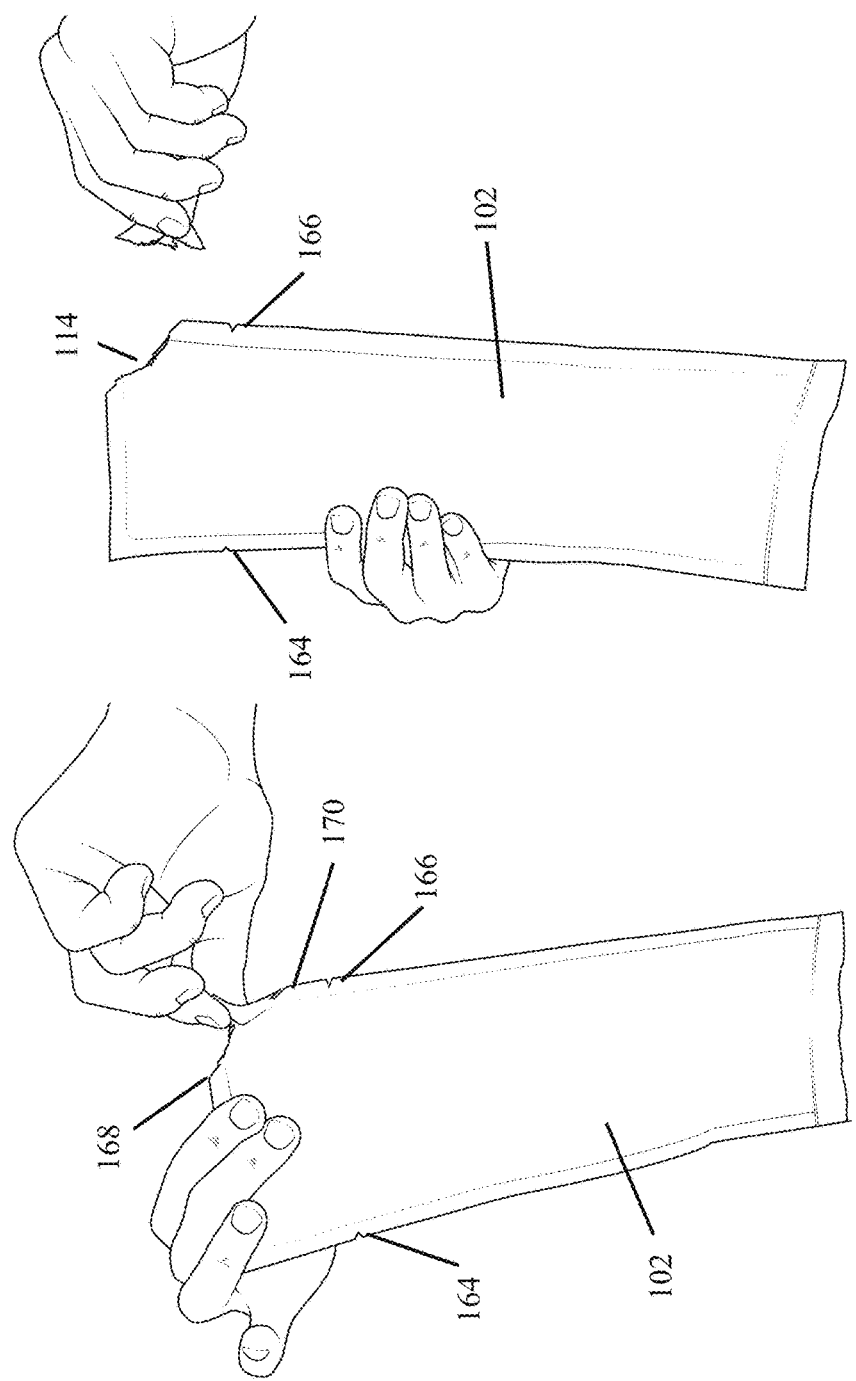

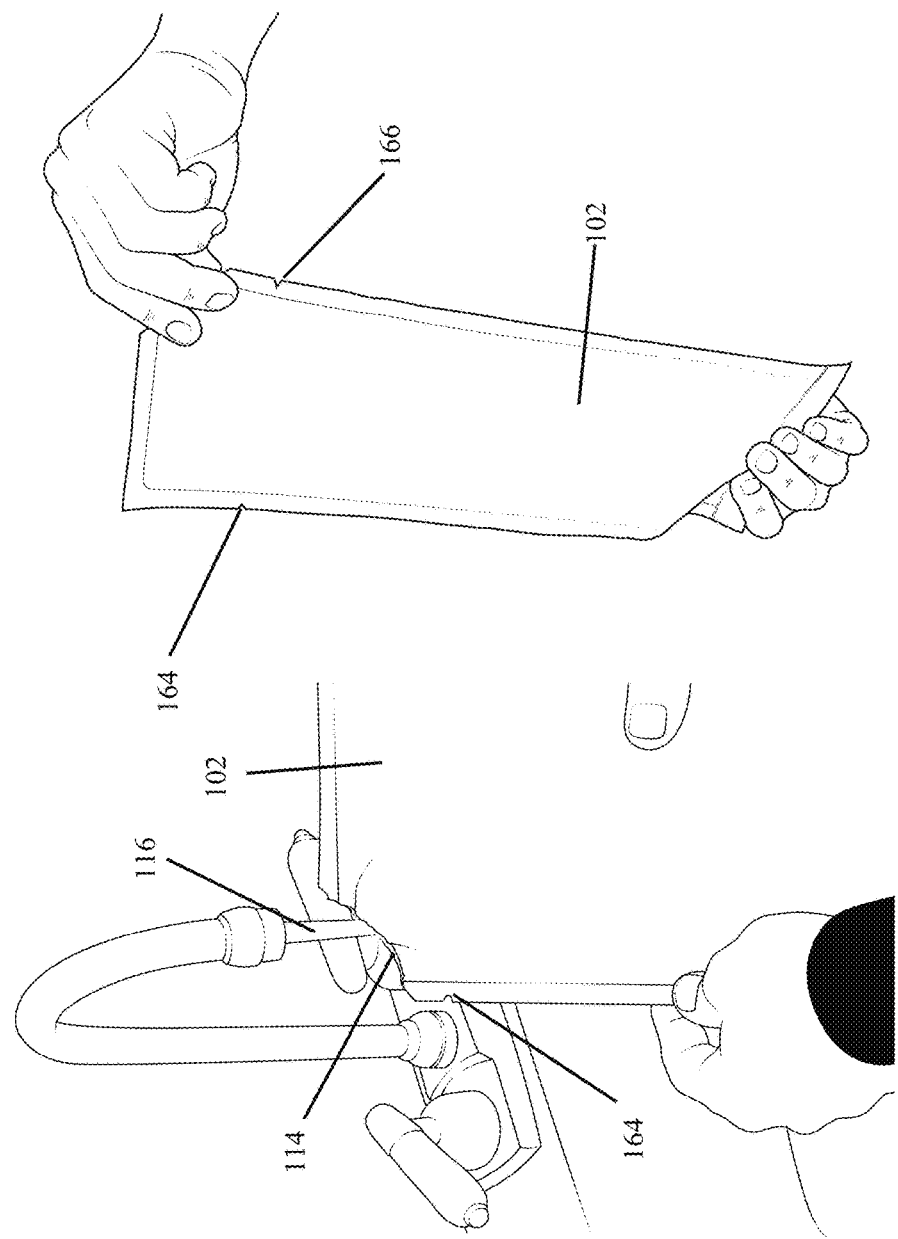

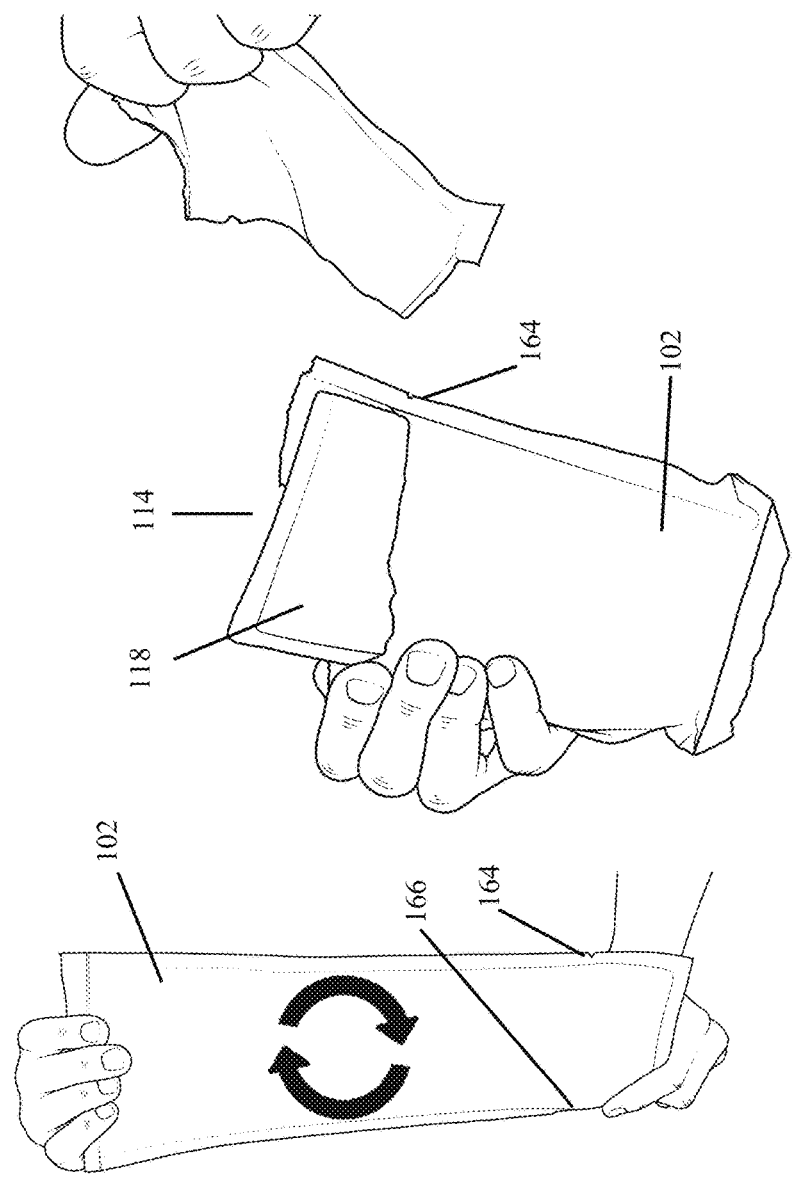

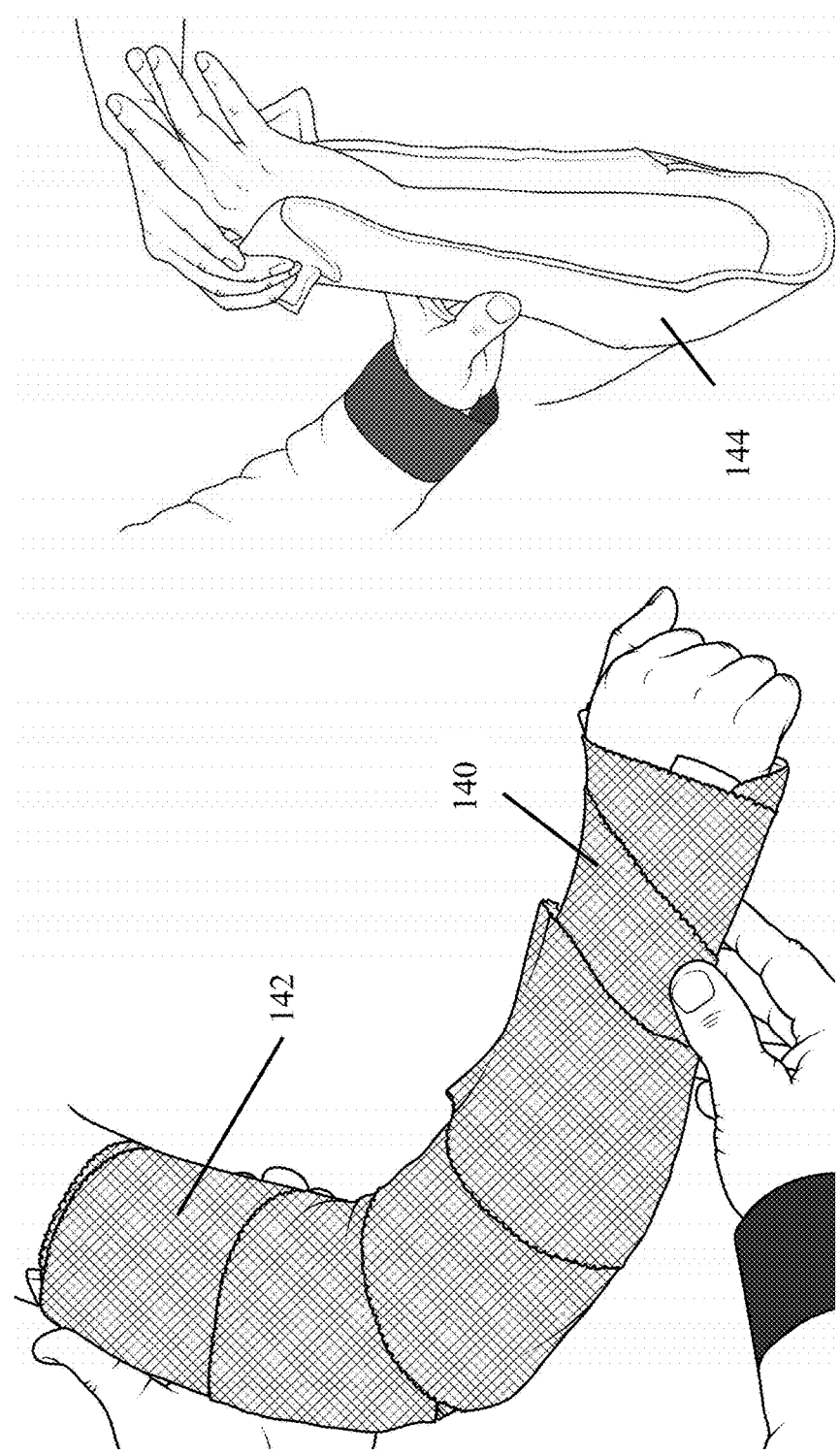

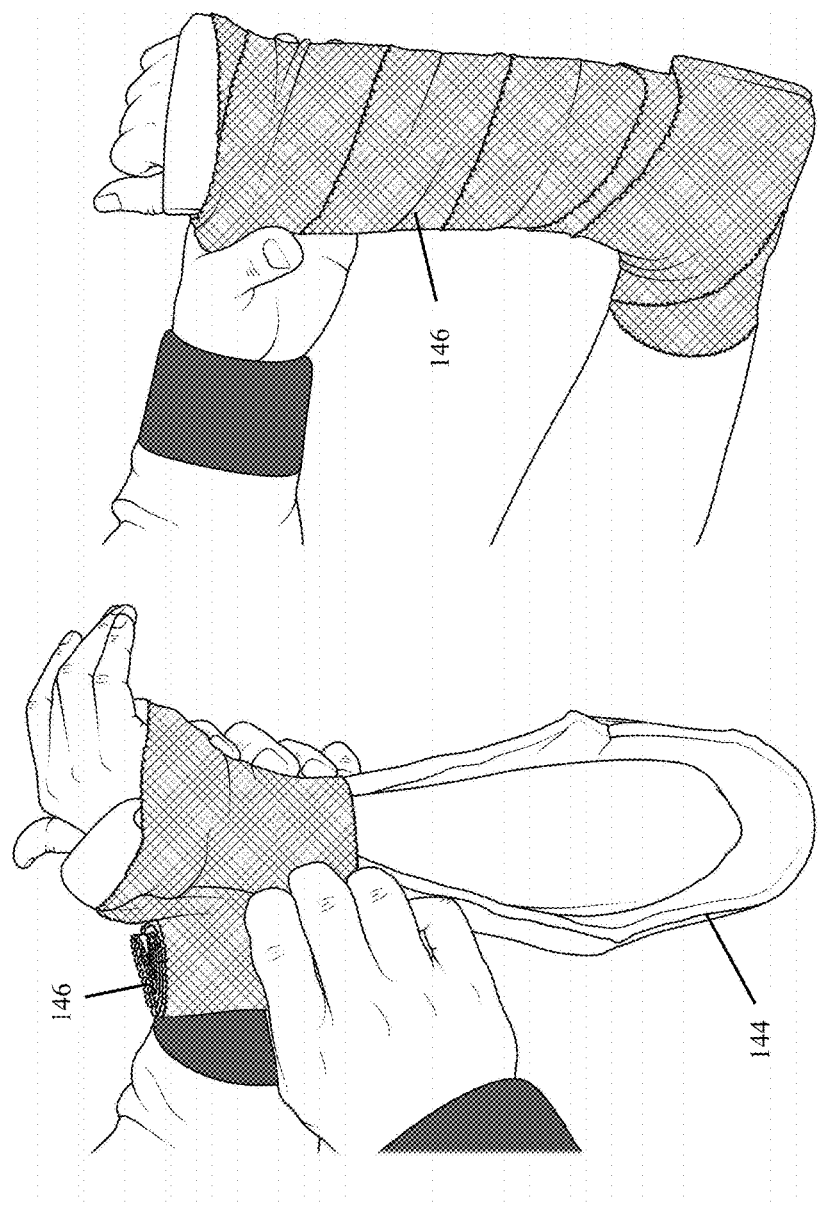

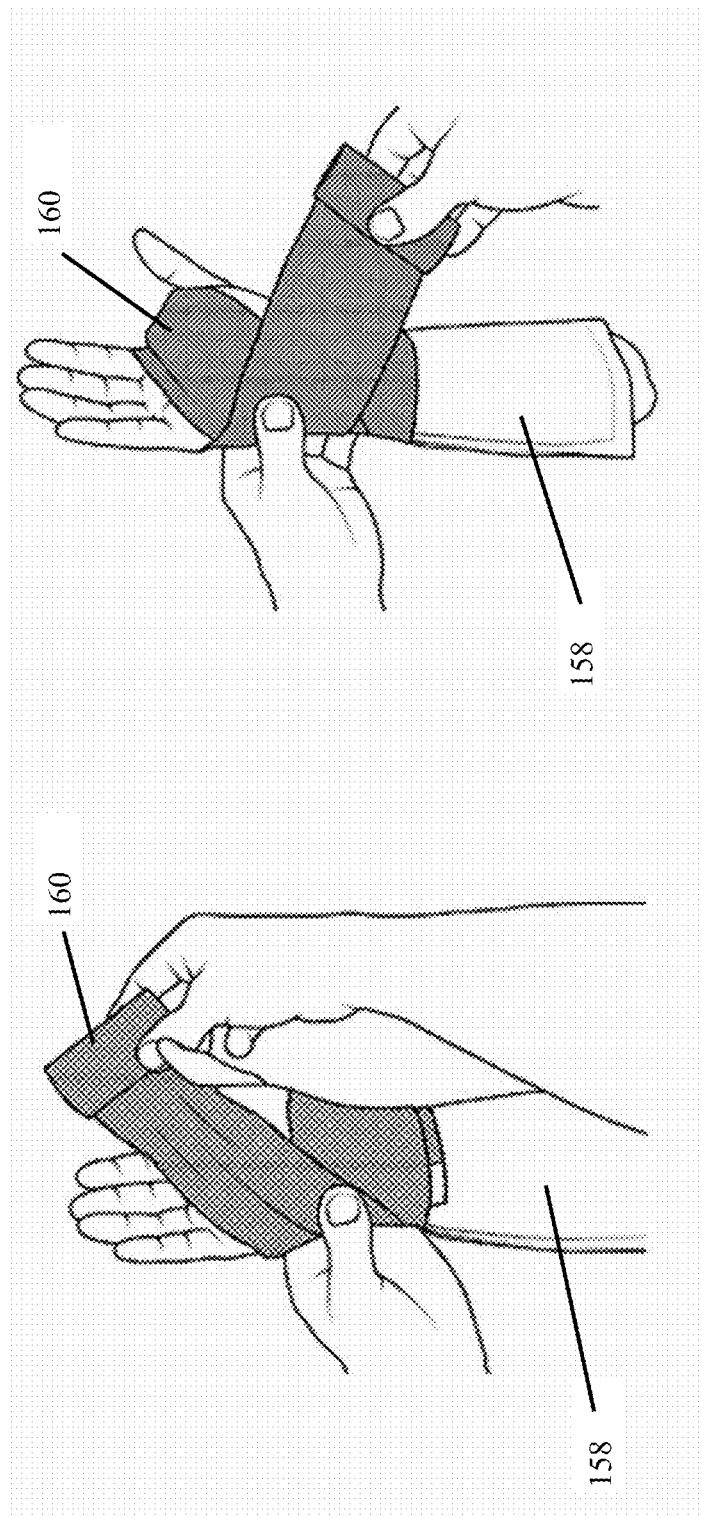

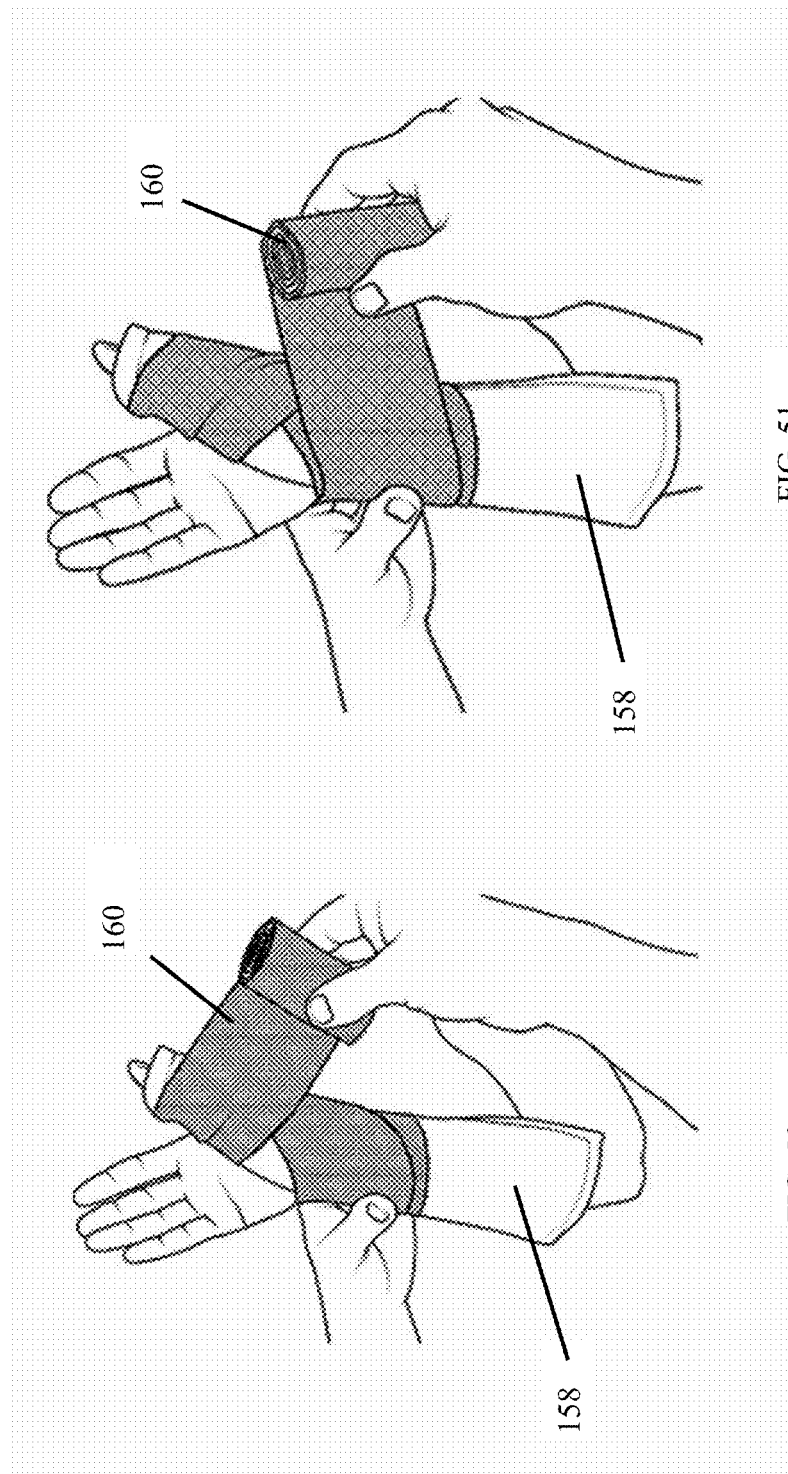

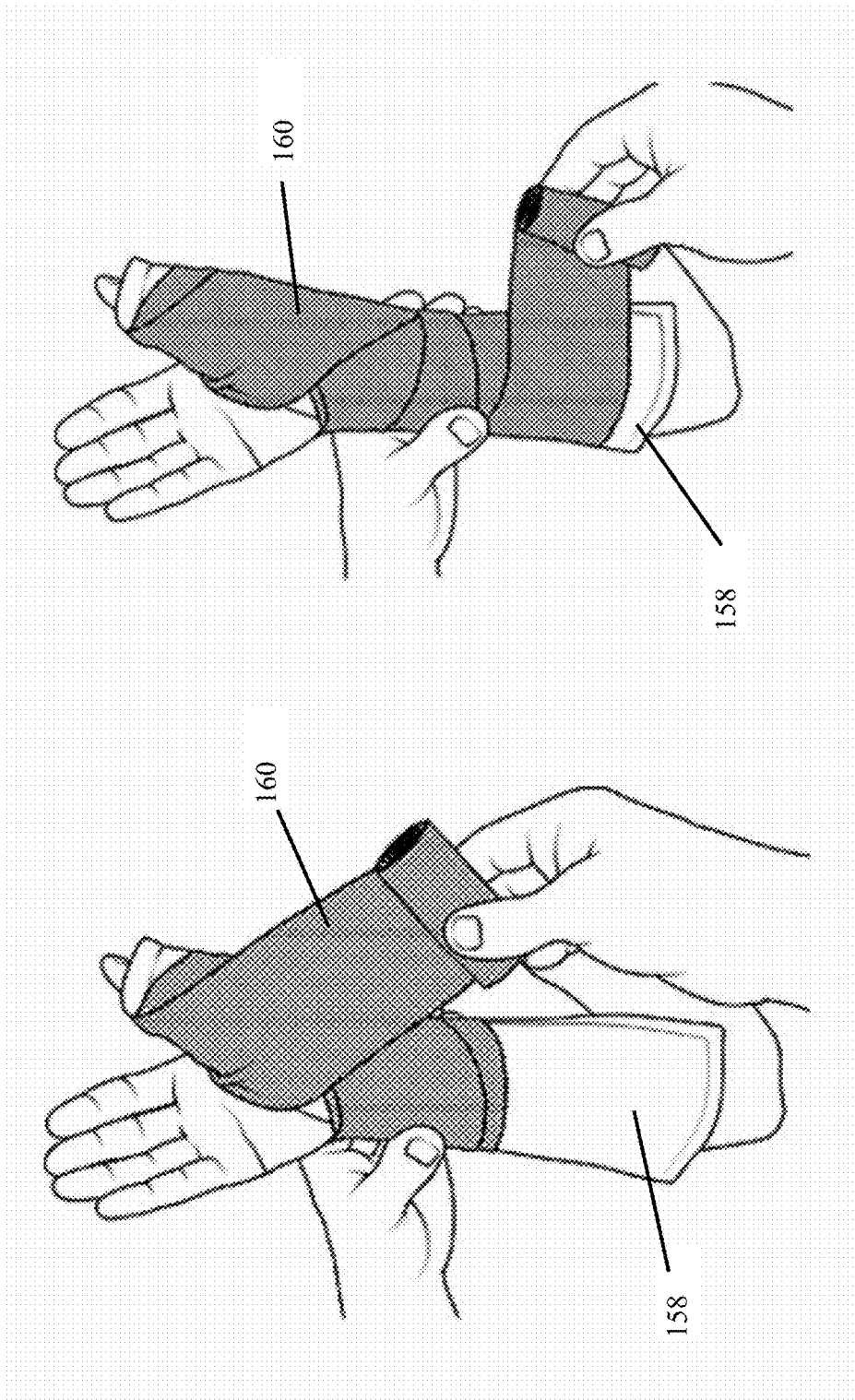

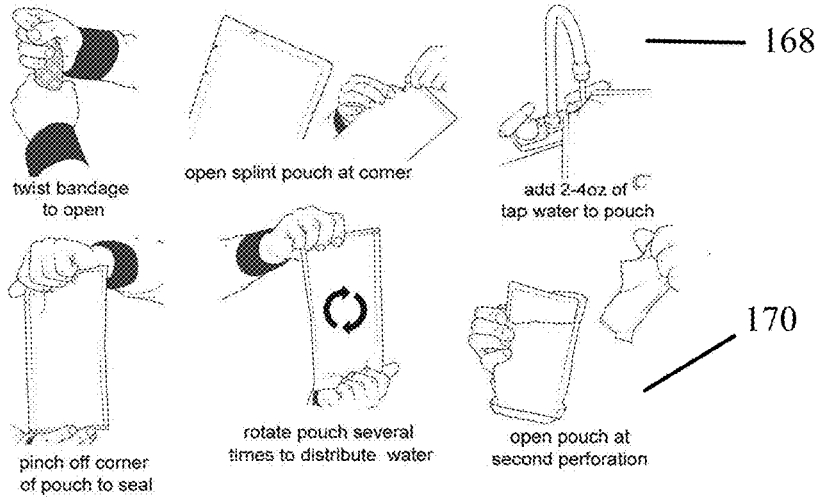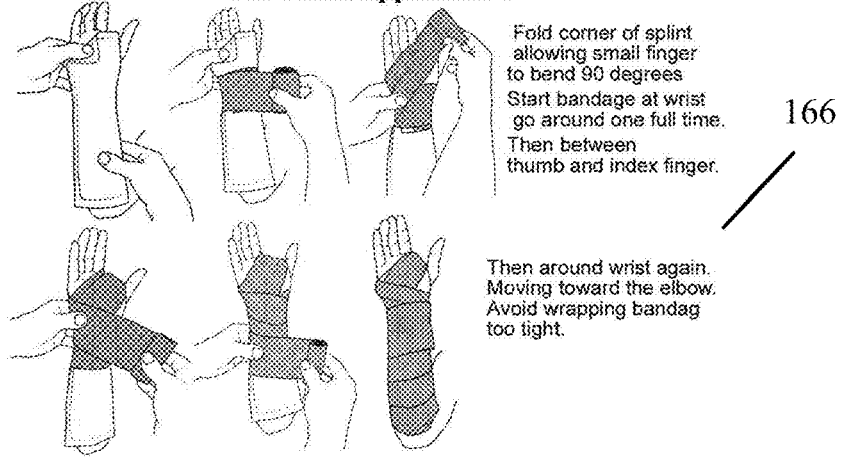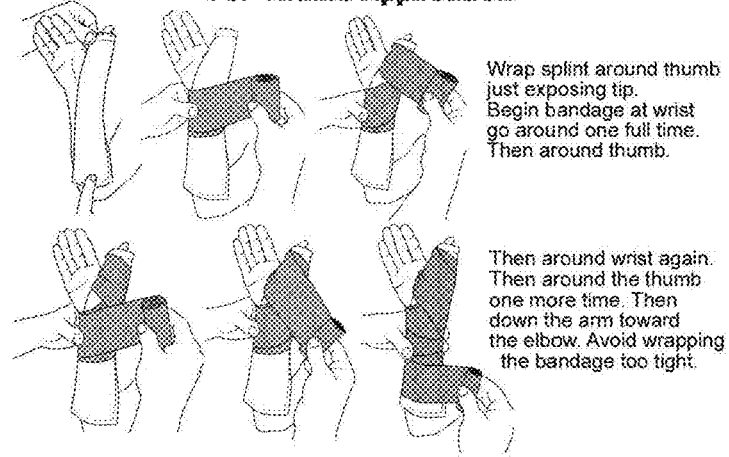
FIG. 55

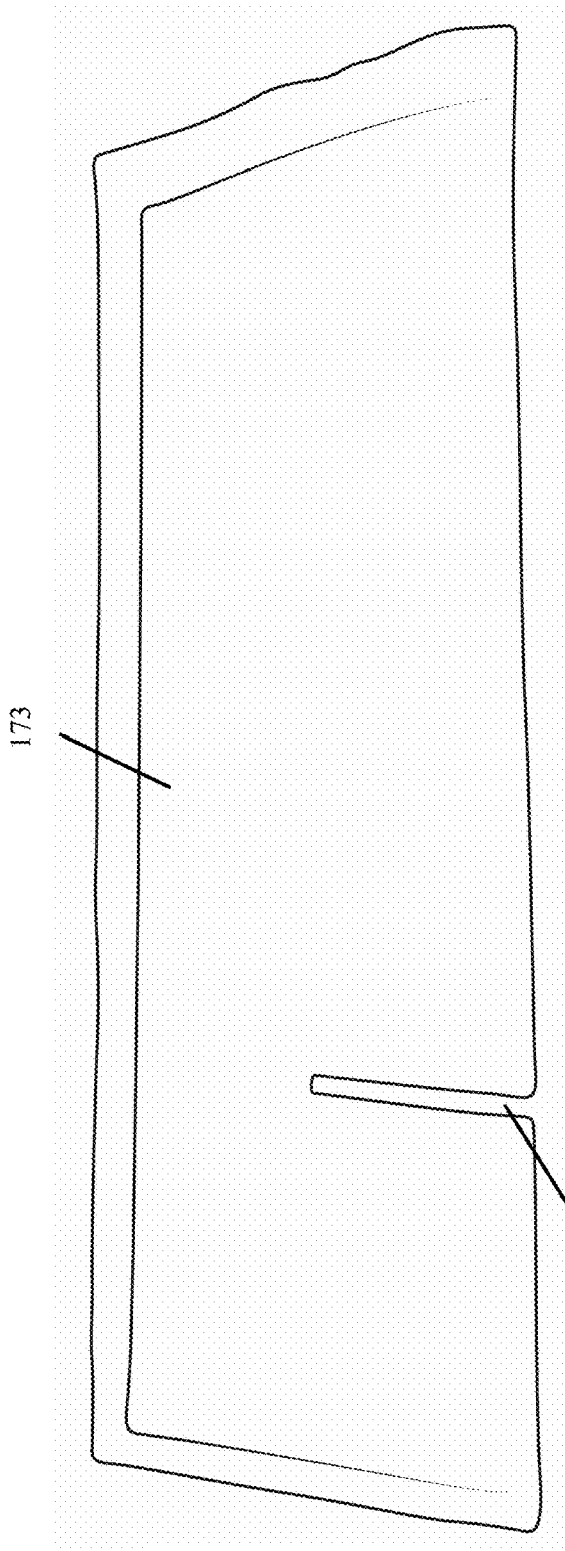

SPLINT KIT SET

CROSS-REFERENCE TO RELATED APPLICATIONS

This application claims priority to and is a continuation in part of U.S. patent application Ser. No. 14/447,252 filed on Jul. 30, 2014 entitled Splint Kit Set.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

I. Field of the Invention

This invention relates generally to a splint for treating injuries to an injured person or animal. The present invention is designed to be applied in a hospital, doctor's office, at home, or in the field. The present invention provides a user with the necessary materials to splint an injured person or animal.

II. Description of the Known Art

The present invention relates generally to the field of orthopedic medicine and more specifically to a splint kit. Splints are used in treating and transporting patients who have suffered a bone or joint injury, such as a strain, sprain, fracture, or dislocation. The task of the splint is to stabilize the injured, broken, or fractured body parts quickly to provide comfort, compression, and to prevent further injury and to minimize subsequent treatment and cost of such injuries.

Splints are typically rigid supports made of various substances, such as plaster, fiberglass, plastic, metal, or inflatable materials, which temporarily support an injured extremity. Splints may be held in place by an elastic bandage, hook and loop, or other wrapping. Splints generally do not rigidly encircle a limb to allow for swelling in the early stages of an injury. Typically, splints are applied in an emergency setting. Several components are required and considerable skill is necessary to apply a splint.

Patents and patent applications disclosing relevant information are disclosed below. These patents and patent applications are hereby expressly incorporated by reference in their entirety.

U.S. Pat. No. 7,960,603 issued to Evans on Jun. 14, 2011 ("the '603 patent") teaches a medical bandage that includes a knitted spacer fabric cover or padding positioned in surrounding relation on a moisture-hardenable substrate. A reactive system taught by the '603 patent is applied to and into the thickness of the substrate. The reactive system taught by the '603 patent having a first state wherein the substrate remains in a flexible, conformable condition and a second state wherein the reactive system hardens, simultaneously hardening the substrate into a desired conformation.

U.S. Pat. No. 7,172,565 issued to Termanini on Feb. 6, 2007 ("the '565 patent") teaches a water-curable orthopedic splint, which can be immediately applied to an affected limb includes a water-curable orthopedic casting material, which is in the form of a splint, and a gel container. The '565 patent teaches that the word gel is meant to apply to a viscous semi-solid which can be applied over surfaces in an adherent film and will disperse and move in response to the movement of the practitioner's hands in molding and forming the adhesive bandage around the limb or in the formation of various shapes as splints prior to application to the patient. The '565 patent teaches that it is to be distinguished from a free-flowing liquid which drips when applied to a limb resulting in a messy environment.

U.S. Pat. No. 6,482,167 issued to Grim, et al. on Nov. 19, 2002 ("the '167 patent") teaches a technique for forming orthopaedic splints or supports that includes the steps of impregnating the edges of casting material with non-rigid bonding material and subsequently impregnating the casting material with water hardenable material such as urethane. The edge treatment taught by the '167 patent keeps the edges in a relatively cushioning or non-rigid state to avoid irritation of the skin of the patient. The blanks taught by the '167 patent may be formed using a mold having a groove defining the outline of the casting blank, and a ridge for implementing the impregnation of a bead of bonding material into the casting fabric. The casting blank material taught by the '167 patent may be formed of spacer or double knit type material, or may be formed of several layers of fabric including high strength filaments, and may have padding material as one layer.

U.S. Pat. No. 7,465,283 issued to Grim, et al. on Dec. 16, 2008 ("the '283 patent") teaches a cast or support assembly that includes inner double knit padding material in which the outer layer is woven or knit to have substantial size openings, while the inner layer of the double knit material to be located against the skin of the patient is more closely woven or knit. The '283 patent teaches that additional casting fabric is also provided, with this casting fabric being impregnated with water hardenable material. The outer casting fabric taught by the '283 patent may include openings extending through it, so that the entire cast assembly has ventilation openings allowing air circulation to accomplish rapid drying following wetting of the assembly by sweat, rain, or by swimming, for example.

U.S. Pat. No. 7,972,288 issued to Chabba, et al. on Jul. 5, 2011 ("the '288 patent") teaches a medical bandaging product, including a sleeve formed of moisture-impervious material and sealable to prevent entry of moisture, and a medical material positioned in the sleeve and sealed therein against entry of moisture until use. The medical material taught by the '288 patent is a substrate having two marginal areas of relatively lower modulus yarns and/or a more open knitted structure to provide reduced abrasion against the skin. A reactive system on the substrate taught by the '288 patent remains stable when maintained in substantially moisture-free conditions and hardens upon exposure to sufficient moisture to form a rigid, self supporting structure. The '288 patent teaches that a soft, flexible protective material covers at least one of the major faces of the substrate along its length to provide a cushioning barrier between the substrate and the skin of a patient when the material is in use.

U.S. Pat. No. 7,004,917 issued to Henderson, et al. on Feb. 28, 2006 ("the '917 patent") teaches hardenable orthopaedic supports and methods of making the same. One embodiment taught by the '917 patent provides a support which includes a blank made of a permeable, flexible material and including a structural region impregnated with a hardenable material and a peripheral region which will remain flexible after the hardenable material is hardened. Another embodiment taught by the '917 patent provides a method of manufacturing an orthopaedic support in which a permeable, flexible material is positioned adjacent a recess of a molding element; the flexible material is contacted with a hardenable material; and the hardenable material is placed under pressure in the molding element to impregnate the section of the flexible material with the hardenable material.

SUMMARY OF THE INVENTION

Splinting of an injured limb or joint is a basic first aid technique to provide immobilization and comfort, to prevent further injury, and to minimize swelling. The current state of the art splinting performed in the family practitioner's office, the orthopedic surgeon's office, the urgent care facility, or the emergency room involves the use of a multi-ply fiberglass sheet cut from a continuous roll covered by foam material/felt. The rolls come in widths from 2 to 5 inches, usually 15 feet in length enclosed in a box. The fiberglass roll is enclosed in an air tight envelope to maintain its pliability as air exposure will cause the fiberglass to harden. After cutting a portion of the fiberglass roll, the user must reseal the envelope using a plastic clip. Each cut of the roll exposes the hardening material/fiberglass found within the foam material/felt to air which causes the hardening material/fiberglass to harden. Hardening the material/fiberglass creates waste as the hardened material is rendered useless. The exposure of the hardening material/fiberglass increases the difficulty of applying the splint as the caregiver may need gloves to apply the splint.

The length of the splint to be cut is either estimated based on the body part to be splinted or measured from the limb to be splinted and then cut. The length is often times estimated as the splint is usually doubled back at the ends to prevent the sharp edge and rough fiberglass from irritating the limb. The splinting technique varies greatly due to the training differences in the caregiver applying the splint. The splint may be applied by a physician, a nurse, a medical assistant, or medical personnel. There is a general consensus that there is a proper and uniform method for splinting of the wrist, elbow, knee, and ankle to provide maximum comfort and protection of the limb.

The present invention provides a concise and uniform methodology for splinting of the wrist, thumb, hand, forearm, elbow, ankle, and knee independent of the caregiver applying the splint. Therefore, the splint kit of the present invention can be utilized both at home, in the professional medical setting, at an athletic event, on the field, on the court, or outdoors. Early and appropriate splinting provides immediate first aid, comfort, and allows flexibility in treatment options. The present invention also reduces swelling, controls blood loss, and prevents further injury. In some cases, early treatment may preclude the need for "emergency care". In the medical setting, the splint kits of the present invention provide safe, uniform, concise, convenient, and efficient splinting without waste.

The present invention relates generally to a splint kit that provides the user with all of the materials and equipment required to apply and set a splint. More specifically, the splint kit provides a sealed splint, bandaging, and a water source for setting the splint. Different kits may be needed depending upon the size of the user to which the splint will be applied. The kits may also vary according to the body part to be applied. Sizing the splint based upon the size of the user and the size of the body part(s) to be splinted eliminates the need for the user to size the splint. The splint kit of the present invention provides the user with a mobile splint kit that may be applied in many different environments.

The splint is self-contained in its own packaging to maintain the integrity of the splint. In one embodiment, at least two splints are self-contained in a single packaging to maintain the integrity of the splints. As the splint(s) is/are exposed to moisture, including moisture in the air, the splint may be activated to harden. The packaged splint eliminates contact of the splint with moisture. The splint sealed within the package is sized to be used in a single use. The user will use the entire splint such that no excess splint will remain. Therefore, no unused portions of the splint will require sealing and storing.

Traditional splints are available in roll form packaged within a sealable package. The user cuts the amount of splint material needed from the roll. The user then reseals the roll within the package. When the package is repeatedly opened, moisture enters the package. The exposure hardens the splint material prior to use of the unused roll.

Furthermore, the roll of splint material is formed from a material that is difficult to cut. Traditional splint material therefore requires a special type of scissors for cutting and sizing the splint. The splints of the present invention are sized for a specific use. These single use sized splints of the present invention eliminate requiring the user to size the splint. The user also does not require the specialized scissors for sizing the splint. Furthermore, the sealed splint material designed for single use does not require resealing the packaging. The splint material is thus not activated causing the splint material to harden and waste.

Precut splints are available. However, these precut splints are oftentimes too long or short. Such precut splints often require a user to size the splint for the appropriate body part. These precut splints are not packaged with multiple splints or the necessary materials, including but not limited to the bandages and water supply, to apply the splint. Furthermore, these precut splints are not designated for a particular application.

One embodiment of the present invention provides a precut enclosed splint, which may be sewn. In one embodiment, the splint is fully encased in a felt or foam material in which the edges are closed. The edges may be closed by being sewn or glued shut. The enclosed splint provides a more comfortable experience for the user. The enclosed splint also assists the caregiver applying the splint as the rough edges of the splint are covered. Therefore, the caregiver may avoid wearing gloves when applying and setting the splint.

Water or another substance is usually applied to the splint to activate the splint. As the splint is activated, the splint begins to harden. The user then applies the splint to the injured area to stabilize the area.

The treating user may then apply a bandage to secure the splint to the user. The bandage is packaged in the splint kit. The applied splint then stabilizes the injury thus reducing pain and further injury.

It is an object of the present invention to provide a user with all the necessary material to apply a splint to an injured person or animal.

It is an object of the present invention to maintain the integrity of the splint material.

It is an object of the present invention to seal the splint to prevent moisture from activating the splint.

It is an object of the present invention to size the splint to enable a user to easily apply a splint.

It is an object of the present invention to eliminate the need for a user to manually size the splint.

It is an object of the present invention to provide a sealed water source to be applied to the splint.

It is an object of the present invention to provide a container for a water source that does not require a special tool for opening the water source.

It is an object of the present invention to supply all of the materials needed to apply and set a splint.

It is an object of the present invention to provide precut enclosed splint(s) available in the appropriate length in a single enclosure for the body part to be splinted.

It is an object of the present invention to provide the number of splints needed for each particular body part.

It is an object of the present invention to be sized depending upon the person who will be wearing the splint.

It is an object of the present invention to provide an enclosed splint in which the ends of the splint are enclosed.

It is an object of the present invention to allow a caregiver to avoid wearing gloves when applying and setting the splints.

It is an object of the present invention to provide visual instructions on the packaging and video instructions by website to assist with educating and facilitating the ease of applying the splint.

It is an object of the present invention to provide a portable solution for applying a splint.

It is an object of the present invention to provide a splint that may be applied anywhere.

It is an object of the present invention to provide flexibility in treatment options.

It is an object of the present invention to increase safety by improving immobilization of the user.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 7 is an environmental view thereof;

FIG. 8 is an environmental view thereof;

FIG. 9 is an environmental view of one embodiment of the present invention;

FIG. 10 is an environmental view thereof;

FIG. 11 is an environmental view thereof;

FIG. 12 is an environmental view thereof;

FIG. 32 is an environmental view thereof;

FIG. 33 is an environmental view of one embodiment of the present invention;

FIG. 34 is an environmental view thereof;

FIG. 35 is an environmental view thereof;

FIG. 44 is an environmental view thereof;

FIG. 45 is an environmental view thereof;

FIG. 50 is an environmental view thereof;

FIG. 51 is an environmental view thereof;

FIG. 52 is an environmental view thereof;

FIG. 53 is an environmental view thereof;

FIG. 55 is a front view of instructions of one embodiment of the present invention;

FIG. 56A is a front view of a splint of one embodiment of the present invention;

DETAILED DESCRIPTION

Figure 1:
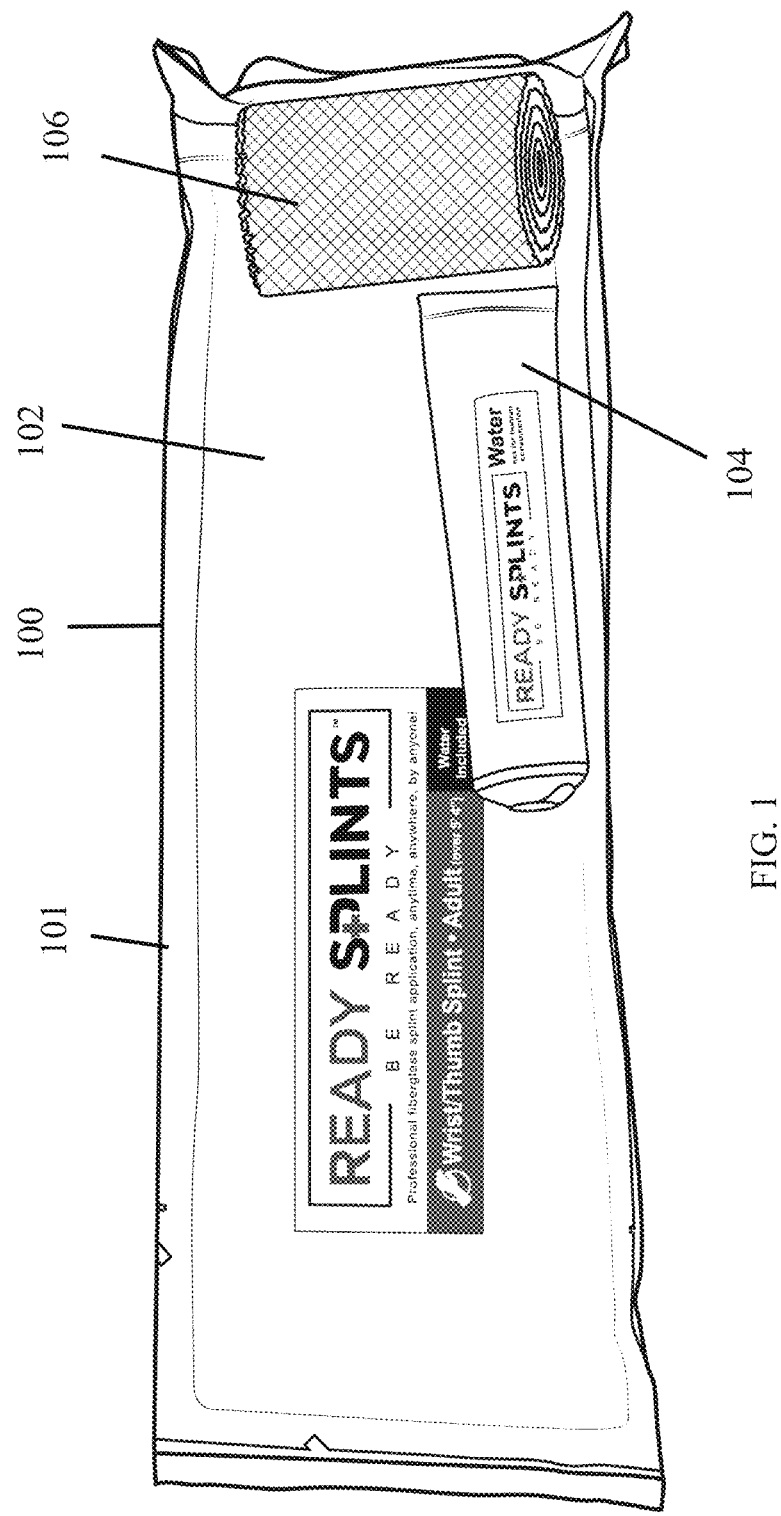
FIG. 1 is a front view of one embodiment of the present invention.

The present invention relates generally to a splint kit 100 shown in FIGS. 1-4 that provides the user with all of the materials and equipment required to apply and set a splint, including but not limited to a fiberglass splint. The splint kit 100 of the present invention provides the user with a mobile splint kit that may be applied in many different environments. The materials needed to apply and set the splint are packaged in a first housing 101, such as a packaging. More specifically, the splint kit 100 provides a sealed splint 102 that is sealed within a splint housing 102, bandaging 106, and a water source 104 for setting the splint. Different kits may be needed depending upon the size of the user and the body part to which the splint will be applied. The sized splints eliminate the need for the user to size the splint. Therefore, the sized splint allows the user to apply and set the splint without cutting or otherwise adjusting the size of the splint.

The number of splints packaged within splint kit may vary according to the body part to be set. For example, the boxer kit, forearm kit, and the wrist/thumb splint kit may be packaged with one splint. The ankle splint kit, elbow splint kit, and knee kit, on the other hand, may be packaged with two splints, wherein each splint may vary in width and/or length. Each kit provides the appropriate number of splints required to stabilize the injured body part.

In one embodiment, all splints of each kit are stored within a single splint housing 102. In another embodiment, each splint may be stored in individual splint housing 102. Storing the splints within one splint housing 102 simplifies the application of water to the splints. Providing one splint housing 102 storing multiple splints removes the need to ration the water to each splint if the splints were stored in multiple splint housings. Each splint housing 102 stores the splint(s) within an airtight seal on the splints to maintain the integrity of the splints.

Figure 2:
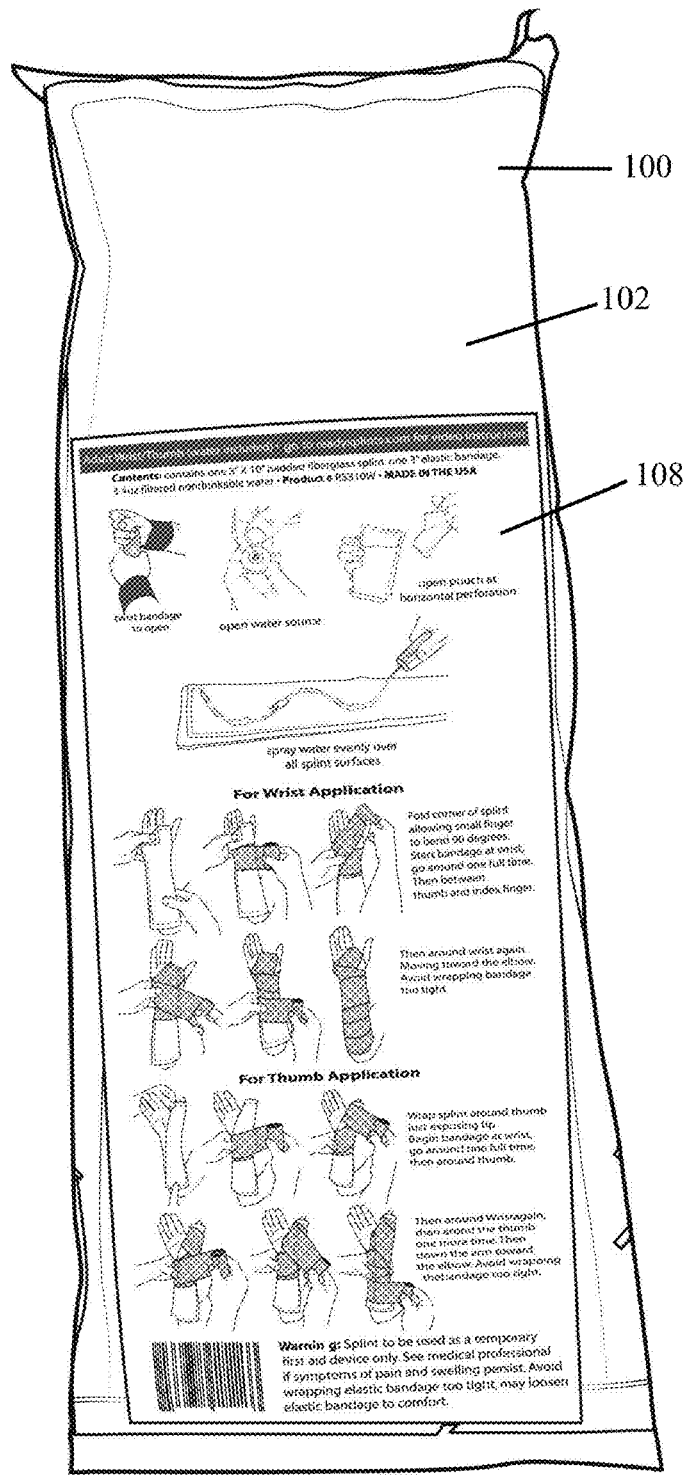
FIG. 2 is a rear view thereof.
Figure 3:
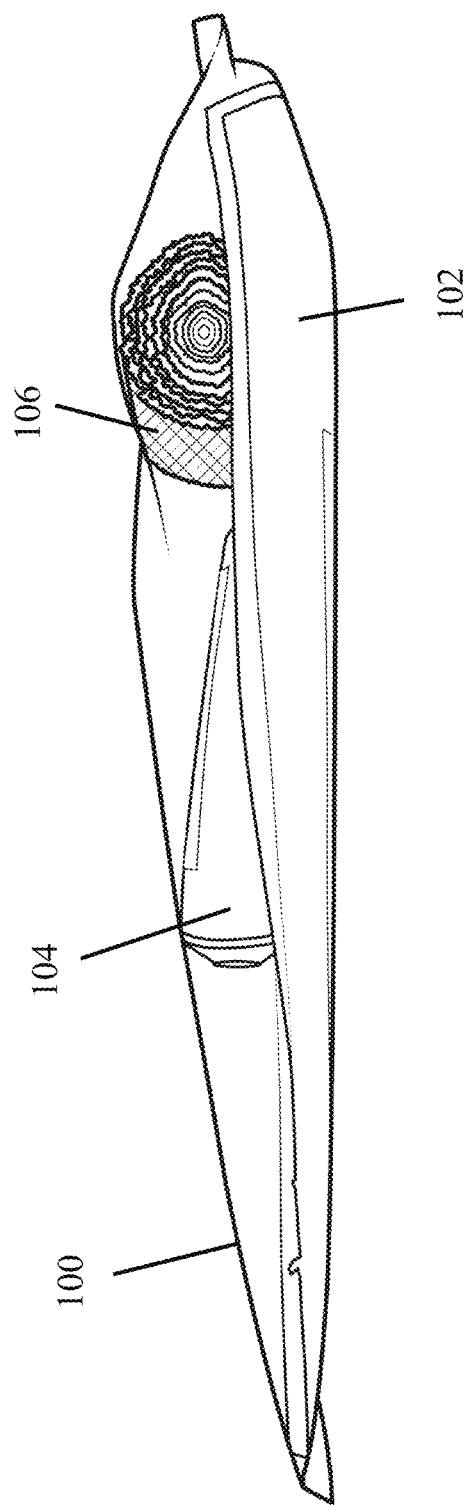
FIG. 3 is a top view thereof.
Figure 4:
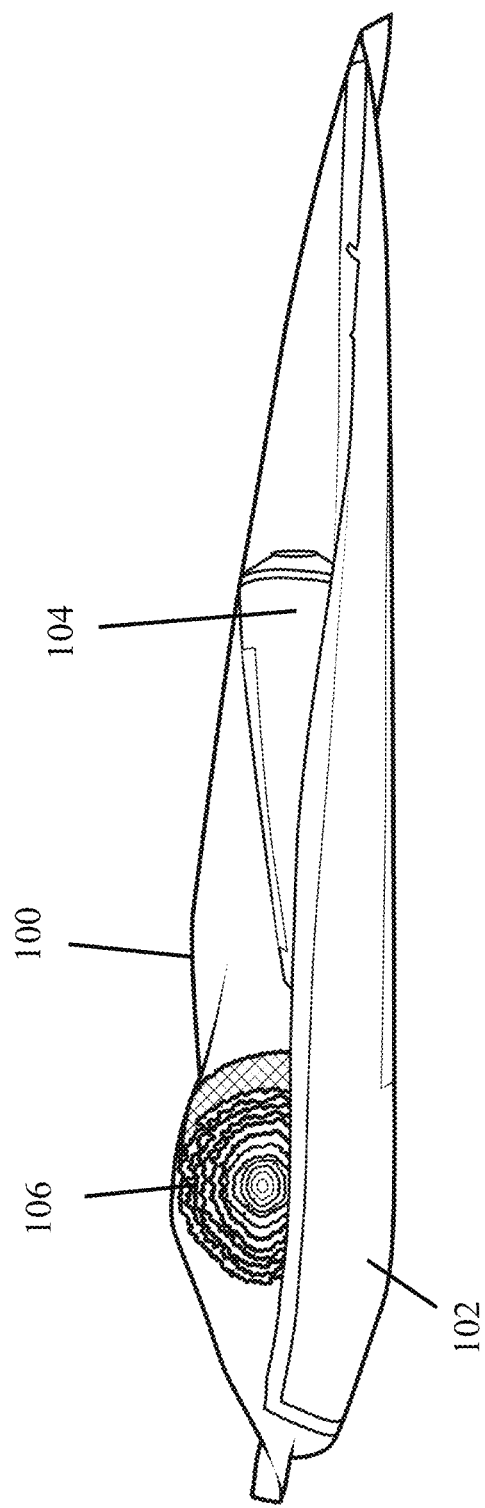
FIG. 4 is a bottom view thereof.

FIG. 2 shows the rear of the splint kit 100. The kit 100 provides a set of instructions 108 informing the user the method to apply and set the splint. The instructions 108 may also provide drawings such as those shown in the figures showing the proper method in to apply and set the splint. The instructions 108 may be inserted into housing 101 or may be attached to the housing 101.

Figure 13:
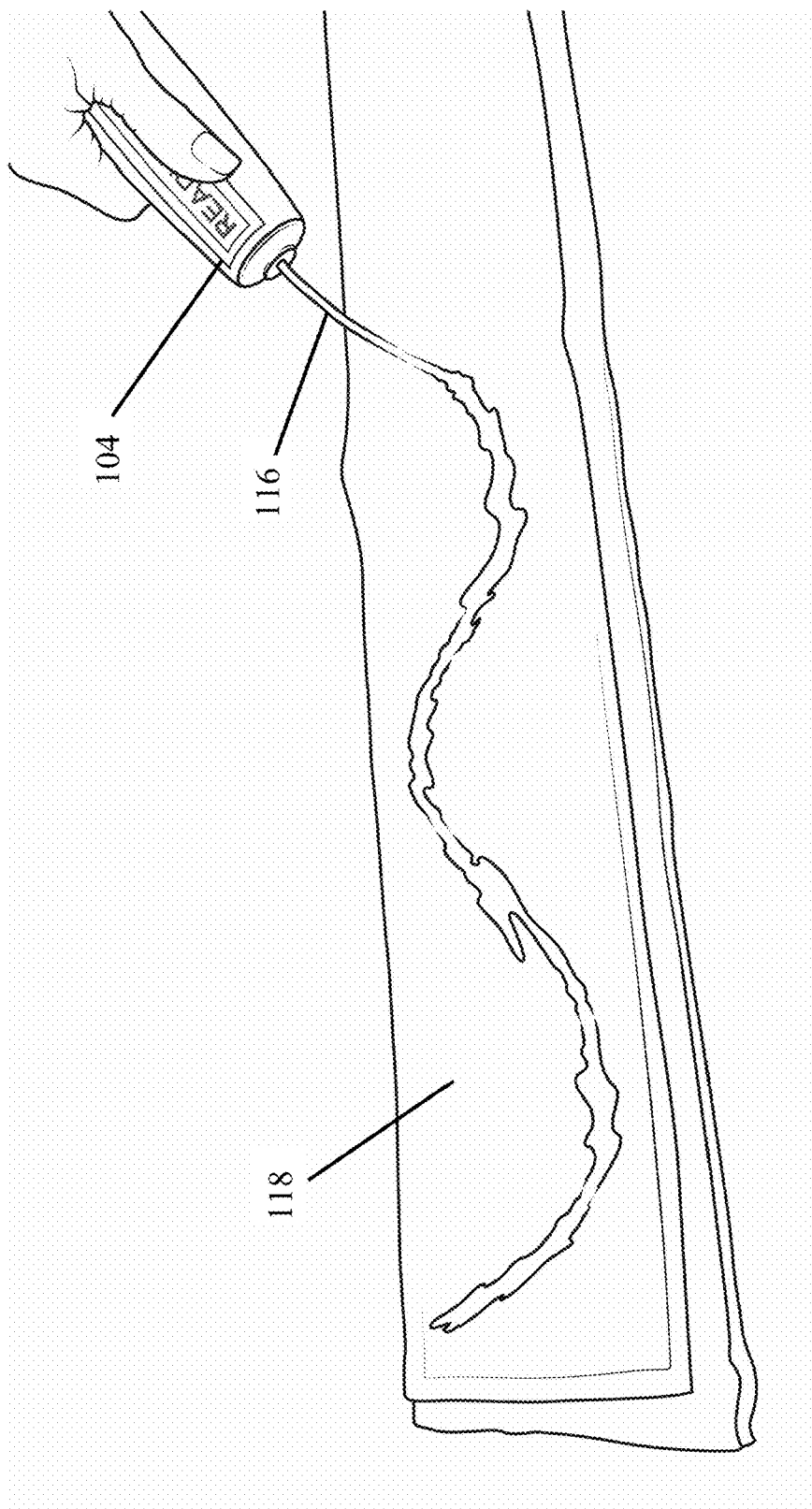
FIG. 13 is an environmental view of one embodiment of the present invention.

FIG. 1 shows one embodiment of the water source 104. Water source 104 provides a flexible housing for storage of the water. In one embodiment, a seal is placed over an aperture in the water source 104 to store the water. The flexible housing allows the user to squeeze the housing to apply the water to the splint. In one embodiment, the splints are removed from the splint housing 102 and the water is applied to the splints as shown in FIG. 13 as discussed below.

In another embodiment, the user may simply apply water into splint housing 102 as shown in FIG. 9. FIG. 9 shows the use of a faucet. Water from water source 104 may be substituted for the faucet.

The water source may be a container with a hinged top that can open and close to allow the contents of container to flow from the container. The lid can close for storage of the contents of container. The lid of one embodiment may be removed entirely, such as a screw-top lid, for accessing the contents of container.

Figure 5:
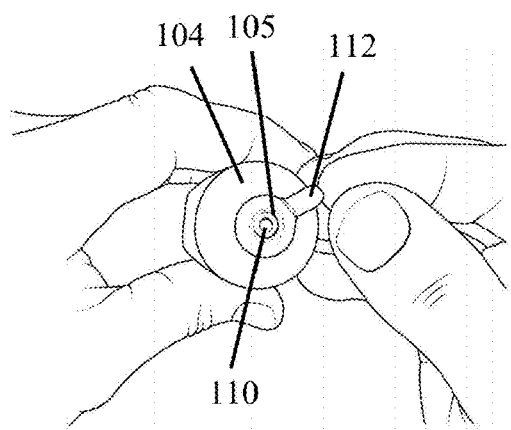
FIG. 5 is an environmental top view of a water source housing of one embodiment of the present invention.

FIG. 5 shows a water source 104 of one embodiment of the present invention. The water source 104 stores water to be used in applying the splint. The housing of the water source 104 includes a release finger 112 located on top 110, such as seal 105, that enables the user to open top 110 of the water source 104 to apply the water. Removal of the top 110 creates an opening from which the water may flow. Once open, the user may apply the water to the splint to activate the splint. In one embodiment, the splint is stored within a second housing. The water from the water source may be placed into the second housing for application to the splint as will be described below.

Figure 6:
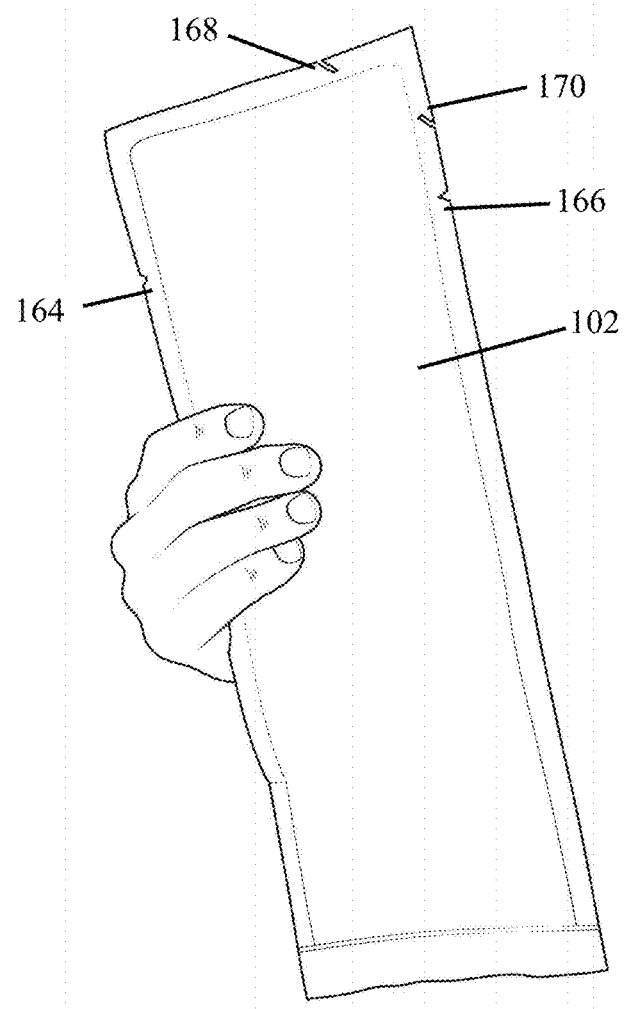
FIG. 6 is an environmental view of a splint housing of one embodiment of the present invention.

FIGS. 6-10 show one embodiment of the splint housing 102. FIG. 6 shows the splint housing 102 that seals the splint. The splint is stored in a moisture-tight housing 102 that limits the splint's contact with moisture. The splint is self-contained in its own packaging to maintain the integrity of the splint. As the splint is exposed to moisture, including moisture in the air, the splint is activated and begins to harden. The packaged splint stored within housing 102 eliminates contact of the splint with moisture. The splint sealed within the housing 102 is sized to be used in a single use. The user will use the entire splint such that little to no excess splint will remain. Therefore, the unused portions of the splint will not be required to be sealed and stored.

Referring to FIGS. 6-10, the splint housing 102 provides a first notch set, notches 168, 170, and a second notch set, notches 164, 166. Notches 168, 170 are located at a corner of housing 102 to assist the user in removing a corner portion of the housing 102. The second notch set, notches 164, 166 are located exterior of the corner and the first notch set, notches 168, 170. The user tears the corner of the housing 102 to remove the corner section at notches 168, 170 as shown in FIGS. 7 and 8. Removal of corner section forms a first opening 114 as shown in FIG. 8.

By removing the corner section, water may be introduced by an external source such as a faucet. The user may then pinch the corner as shown in FIG. 10 and invert and/or agitate the pouch to distribute the water while reducing leakage of the water from the pouch. The splint housing 102 provides a second set of notches, opening notches 164, 166. Notches 164, 166 remain present on housing 102 after the removal of the corner section at notches 168, 170. Notches 164, 166 provide the user with an opportunity to enlarge opening 114 in housing 102 as shown in FIG. 12. However, the user should first add water into the splint housing 102 prior to enlarging the opening 114.

The user opens the splint housing 102 at the first opening notch sets, notches 168, 170 to create opening 114 as shown in FIG. 8. The user then applies water 116 from a water source such as the faucet shown in FIG. 9 or water source 104 into opening 114. The water 116 contacts and activates the splint(s) 118 stored within splint housing 102.

As shown in FIGS. 10 and 11, the user then folds the splint housing 102 onto itself to at least partially close the opening 114 of splint housing 102. Providing smaller opening 114 enables the user to more easily reclose the housing 102 to prevent water from leaking from the housing 102.

The user may then agitate the housing 102 to disburse the water through the housing 102 and the splint or splints 118 inside of housing 102. The agitation of the housing 102 enables sufficient water to be applied throughout the splint(s) 118 to activate the splint(s) 118. After the water has been applied throughout the splint(s) 118, the user may fully open the housing 102 at notches 164, 166 to enlarge opening 114 as shown in FIG. 12. The user can then remove the splint(s) 118 from enlarged opening 114 as shown in FIG. 12.

FIG. 13 shows another method of applying water to the splint 118. Instead of opening the splint housing 102 at notches 168, 170, the user opens the housing 102 at notches 164, 166 to expose splint 118. The user removes the splint 118 from housing 102. The user then applies water 116 from water source 104 to the splint 118. The user applies the water 116 along splint 118 to activate the splint 118 for use. The user may then place the splint 118 in the appropriate location for stabilizing the injury.

The splints of the present invention are available in two different configurations. Each splint may be constructed from fiberglass or other hardening material. The fiberglass is encased in foam material/felt. The splint may have closed ends 124 as shown on splint 122 in FIG. 11. The closed ends 124 of splint 122 eliminate exposed fiberglass. The fiberglass may be a rough and scratchy surface that could irritate a user's skin. The felt encloses the fiberglass thus limiting exposure of the fiberglass. The closed ends 124 limit contact with the fiberglass such that the user will not be irritated by the fiberglass. In one embodiment, the splint 122 has closed ends 124 due to the end being sewn. The ends may be closed by other known methods. The closed ends 124 of splint 122 may also reduce the equipment needed to apply and set splint 122. The caregiver may avoid using gloves when applying splint 122 due to the closed ends 124 encasing the fiberglass.

Figure 15:
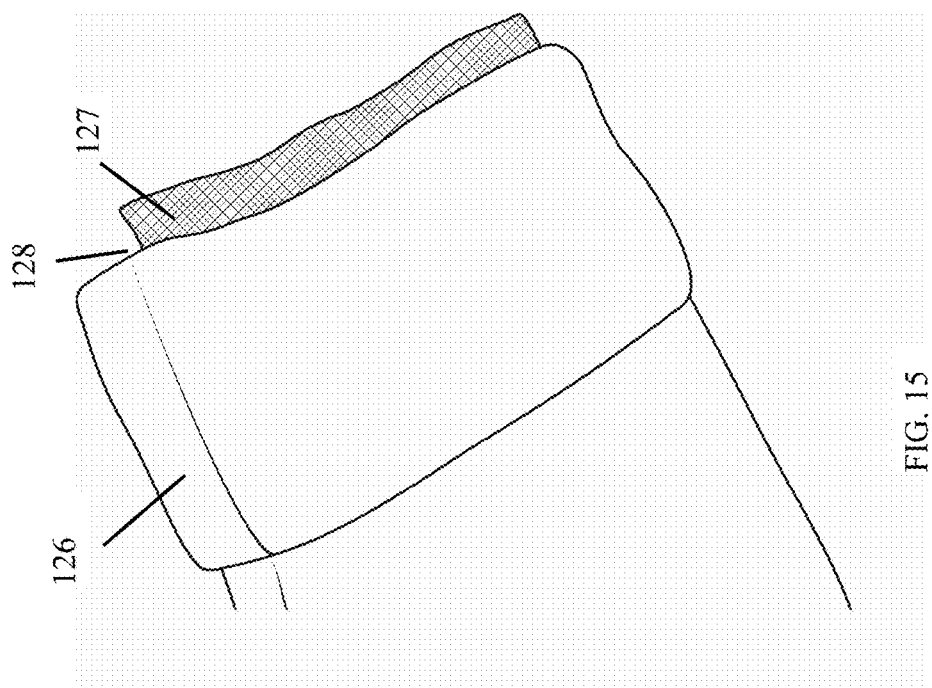
FIG. 15 is a partial view of a splint of one embodiment of the present invention.
Figure 14:
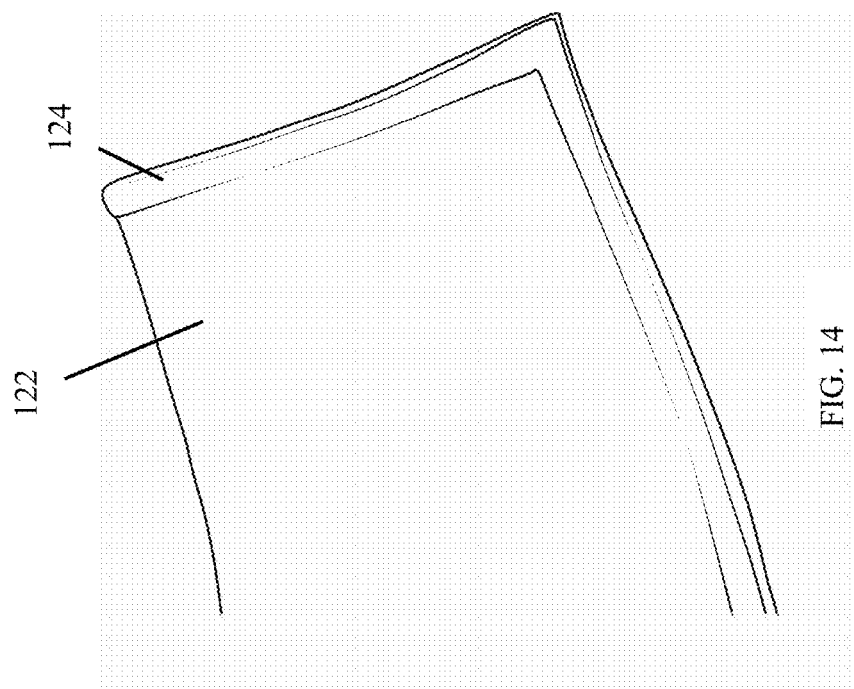
FIG. 14 is a partial view of a splint of one embodiment of the present invention.
Figure 16:
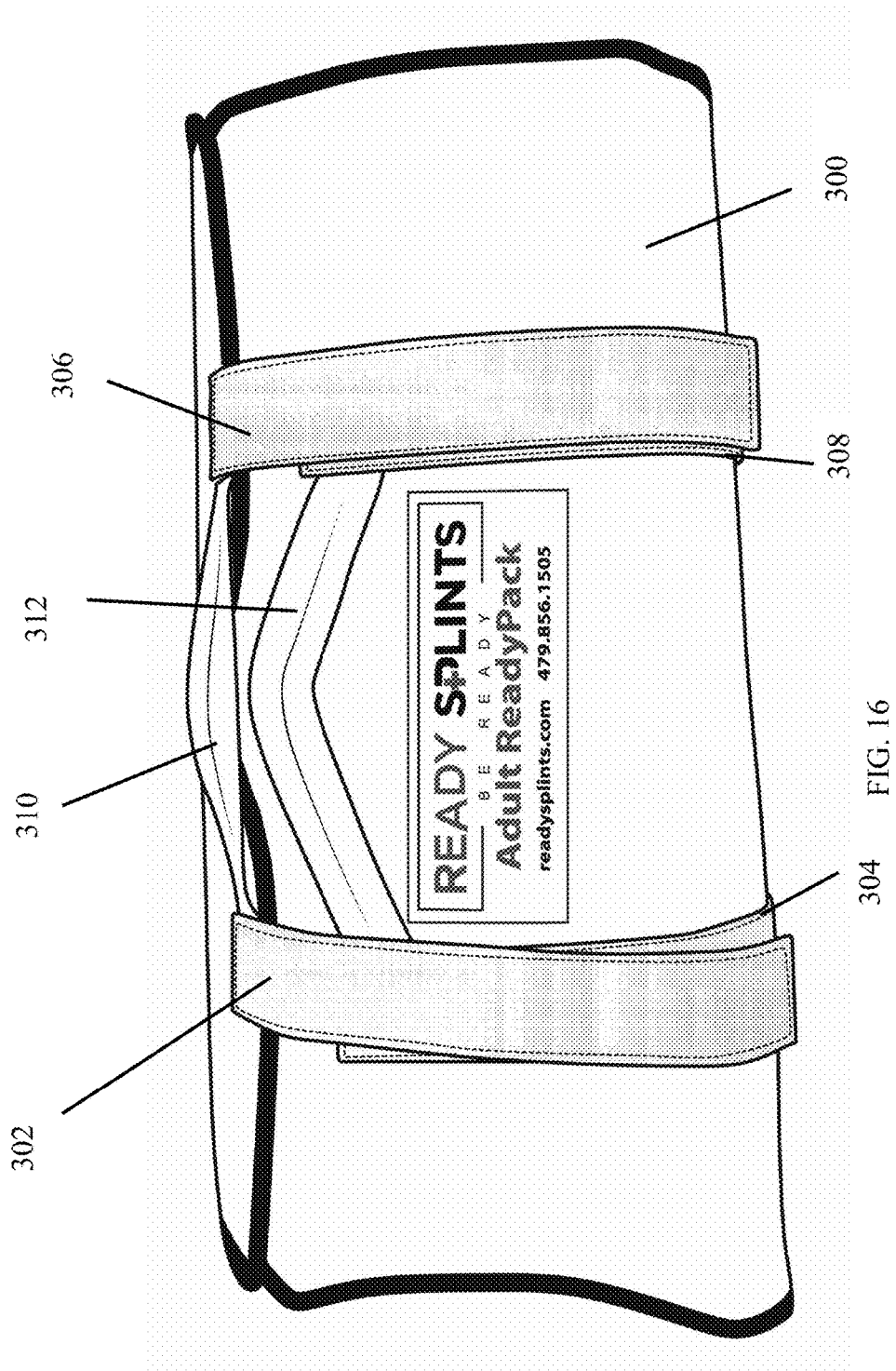
FIG. 16 is a front view of a carrying case of one embodiment of the present invention.

FIG. 15 shows a partial view of the splint 126 in which a portion of the foam material/felt 128 has been removed to show the fiberglass 127 within the foam material/felt 128. To eliminate contact of the rough edge of the fiberglass 127 of the splint 126 with the user, the foam material/felt 128 fully encases the fiberglass 127.

FIGS. 16-20 show a carrying case 300 of one embodiment of the present invention. The carrying case 300 provides multiple compartments for storing the splint kits. The case 300 provides top straps 302, 306 that attach to lower straps 304, 308 to close the case 300. In one embodiment, the straps 302, 304, 306, 308 fasten together via hook and loop fasteners. In another embodiment, the straps may buckle together, tie together, or otherwise secure to one another. The case also provides handles 310, 312 for carrying case 300.

Figure 17:
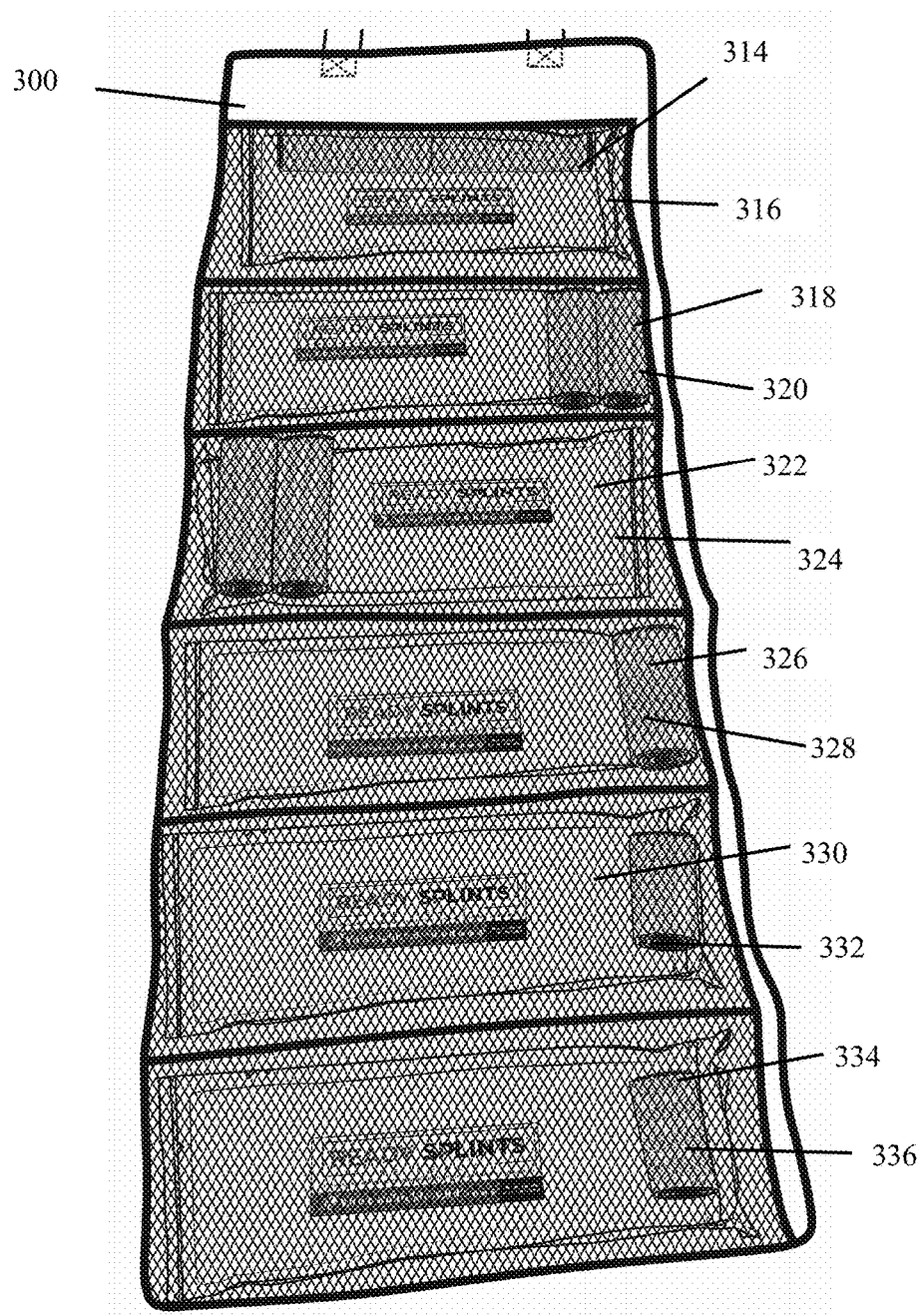
FIG. 17 is an environmental view thereof.

FIG. 17 shows the inside of case 300. The case 300 provides six compartments 314, 318, 322, 326, 330, 334. Each compartment 314, 318, 322, 326, 330, 334 stores at least one kit 316, 320, 324, 328, 332, 336. The kits may include each of the kits described below, including but not limited to an ankle splint kit, an elbow splint kit, a forearm splint kit, a knee splint kit, a wrist/thumb splint kit, and a boxer splint kit. These cases 300 may provide one of each of the splint kits needed for an adult, a teen, or a child. In one embodiment, each case 300 stores an ankle splint kit, an elbow splint kit, a forearm splint kit, a knee splint kit, a wrist/thumb splint kit, and a boxer splint kit in adult sizes. In another embodiment, each case 300 stores an ankle splint kit, an elbow splint kit, a forearm splint kit, a knee splint kit, a wrist/thumb splint kit, and a boxer splint kit in child sizes.

Figure 18:
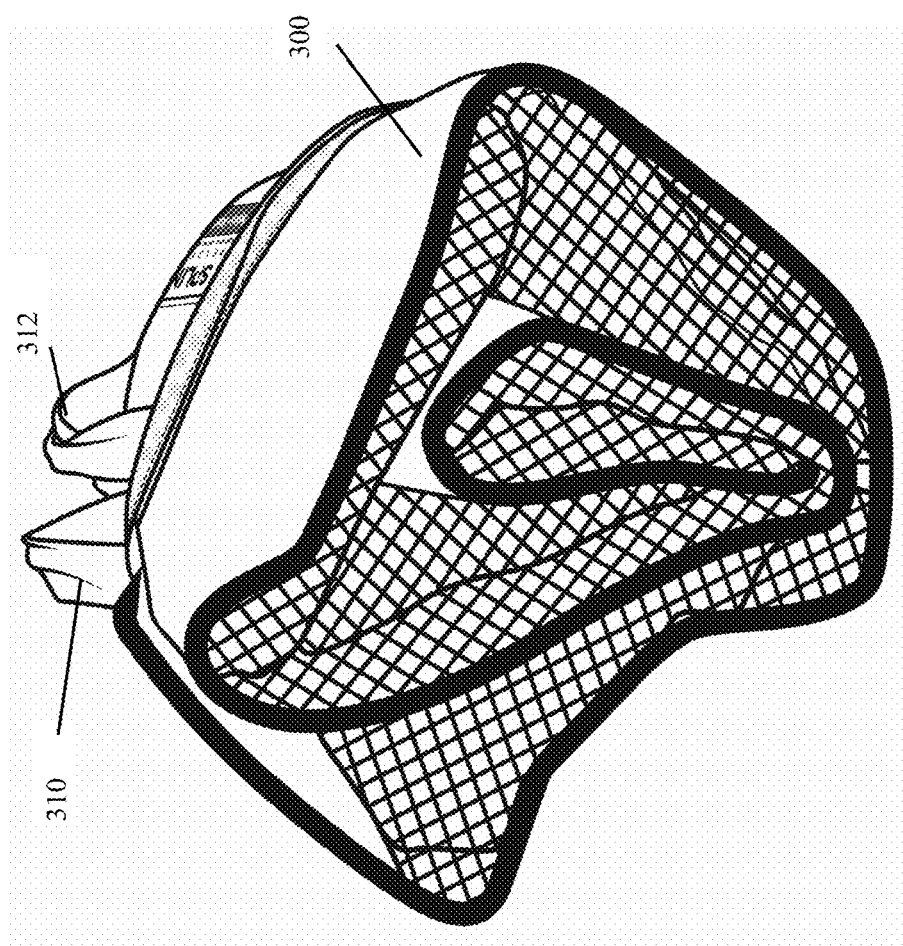
FIG. 18 is a right side view thereof.
Figure 19:
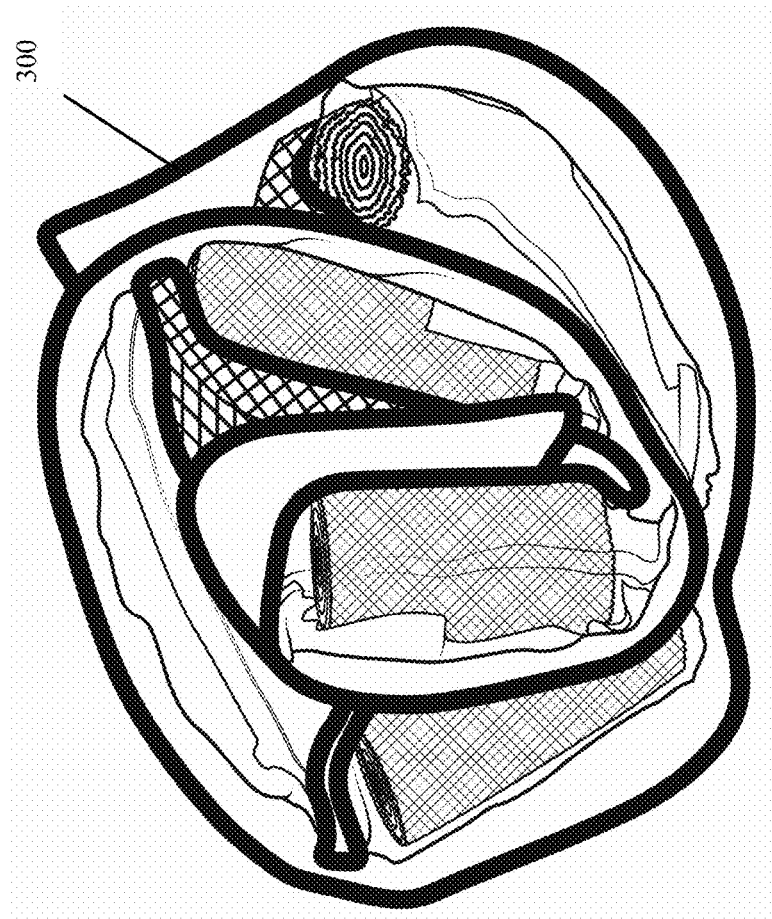
FIG. 19 is a sectional side view thereof.

FIGS. 18 and 19 show the side view with the mesh compartments that store the kits within case 300. Handles 310, 312 simplify the task of carrying the kits.

Figures 20, 21:
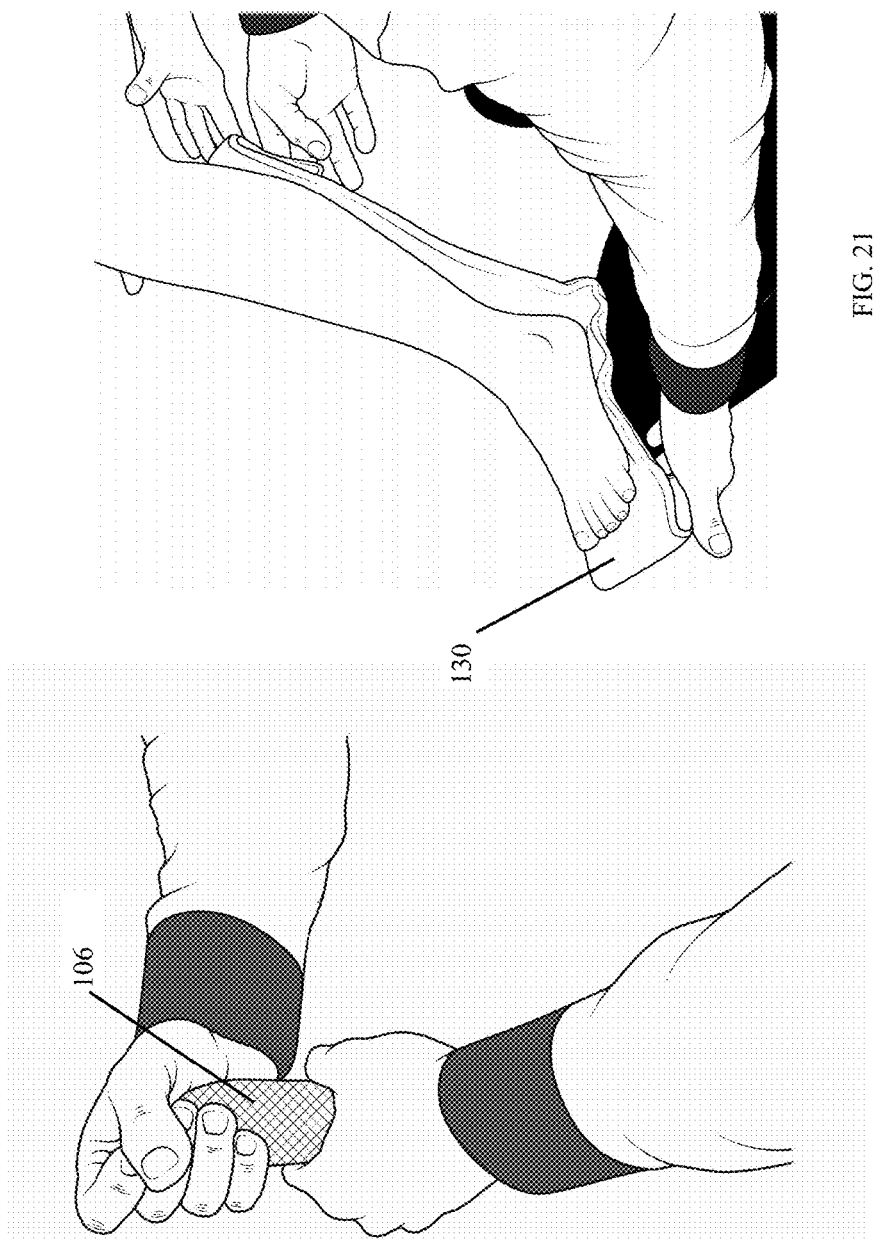
FIG. 20 is an environmental view of one embodiment of the present invention.
FIG. 21 is an environmental view of one embodiment of the present invention.
Figure 23:
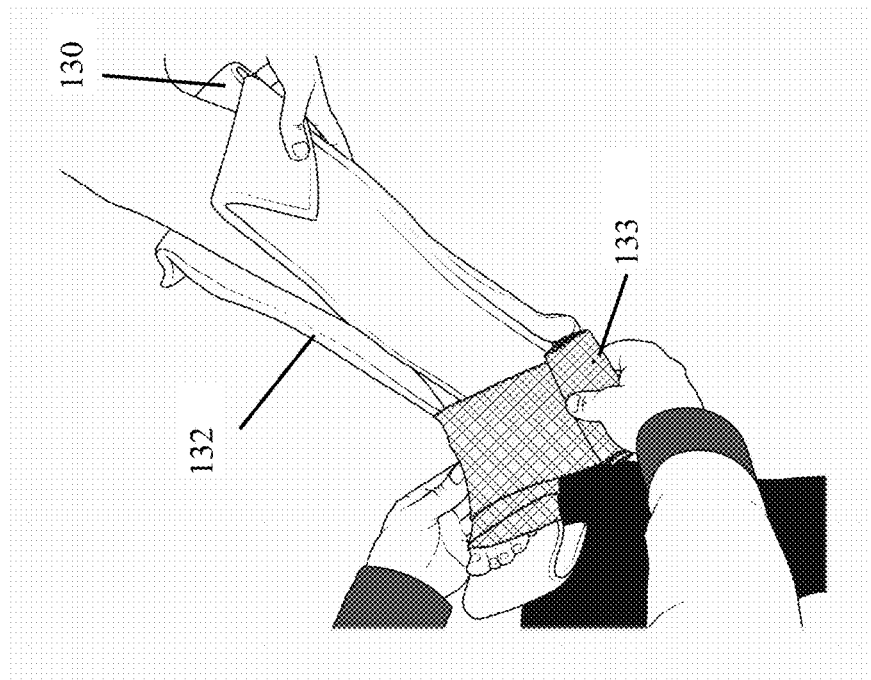
FIG. 23 is an environmental view thereof.
Figure 22:
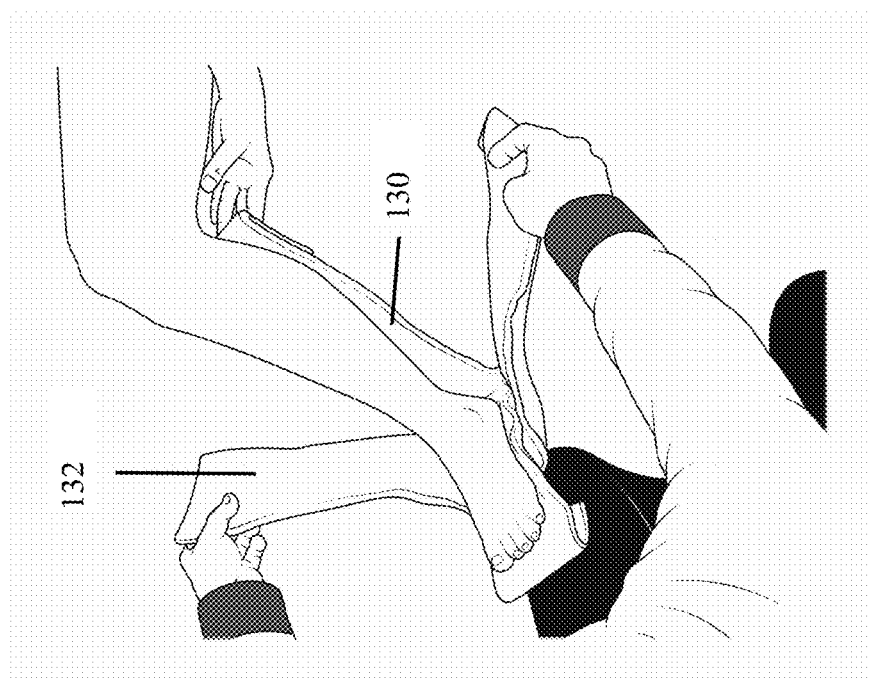
FIG. 22 is an environmental view thereof.
Figure 25:
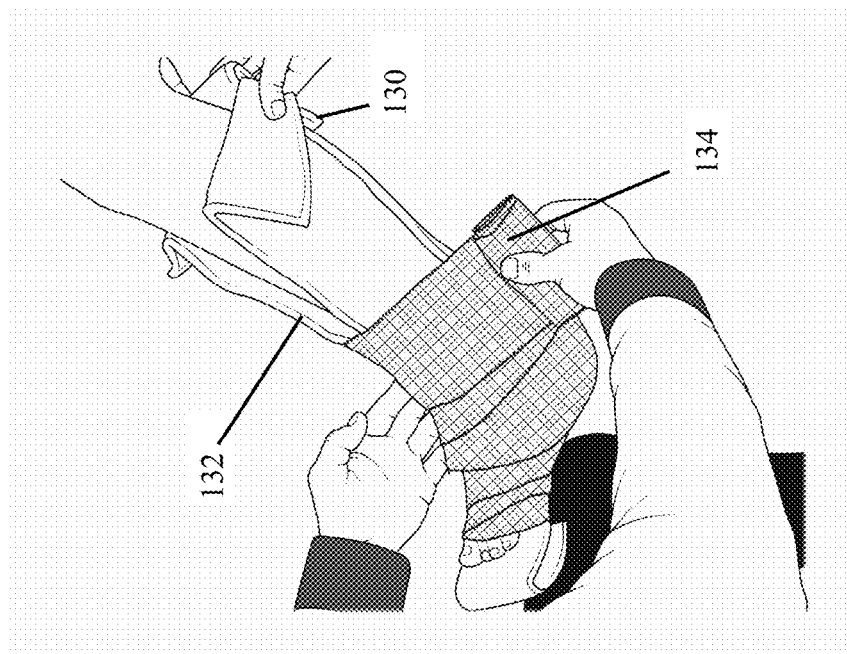
FIG. 25 is an environmental view thereof.
Figure 24:
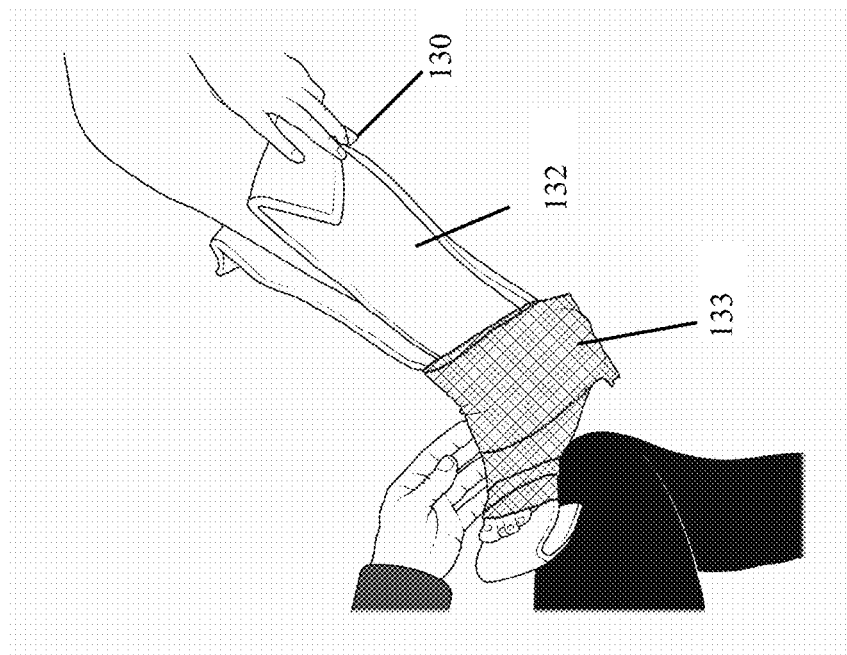
FIG. 24 is an environmental view thereof.
Figure 26:
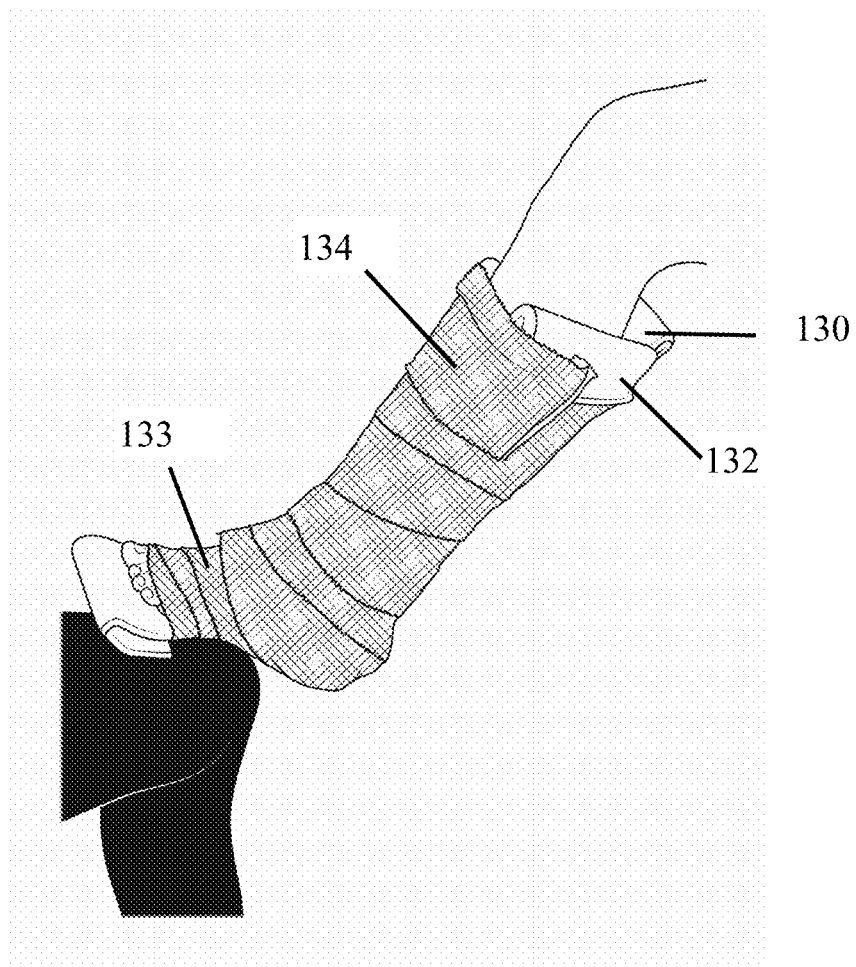
FIG. 26 is an environmental view thereof.
Figure 27:
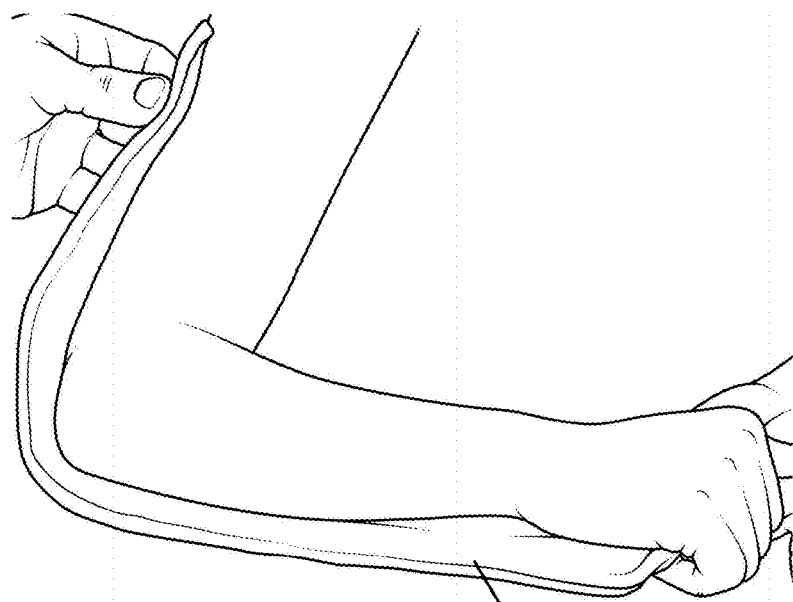
FIG. 27 is an environmental view of one embodiment of the present invention.
Figure 28:
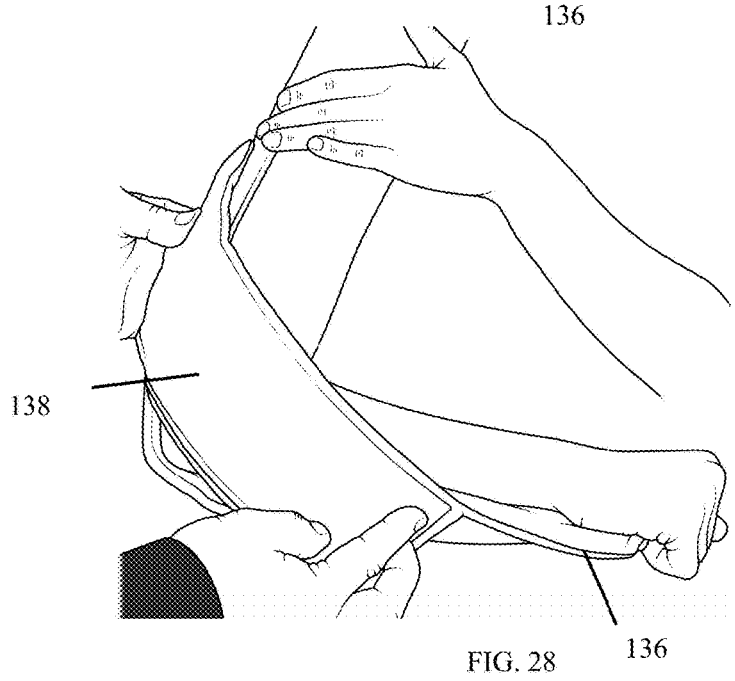
FIG. 28 is an environmental view thereof.
Figure 29:
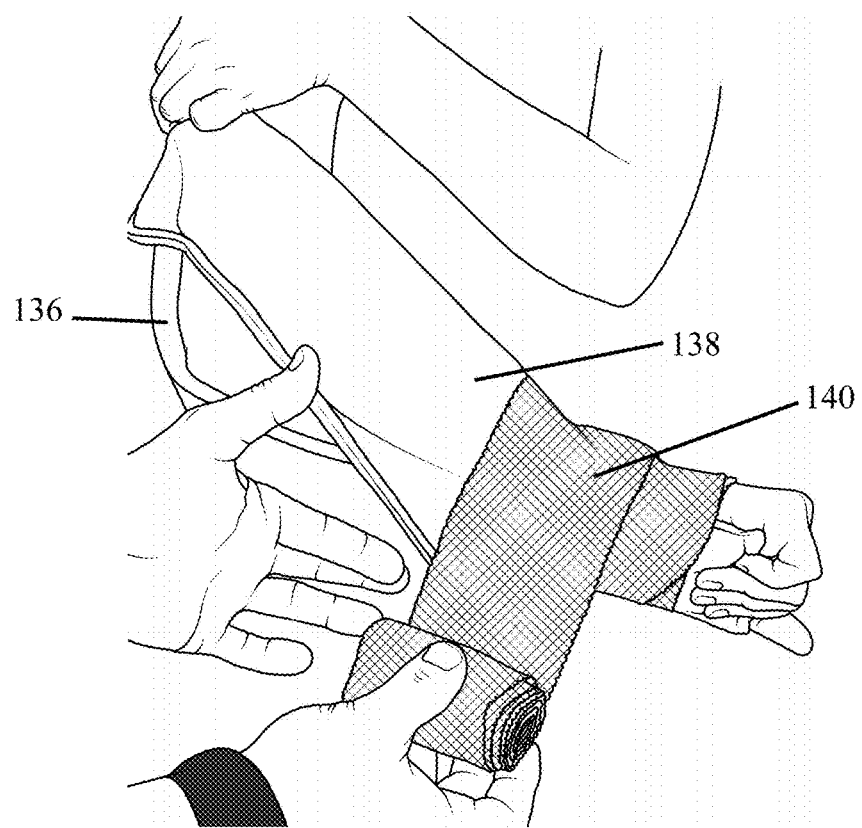
FIG. 29 is an environmental view thereof.
Figure 31:
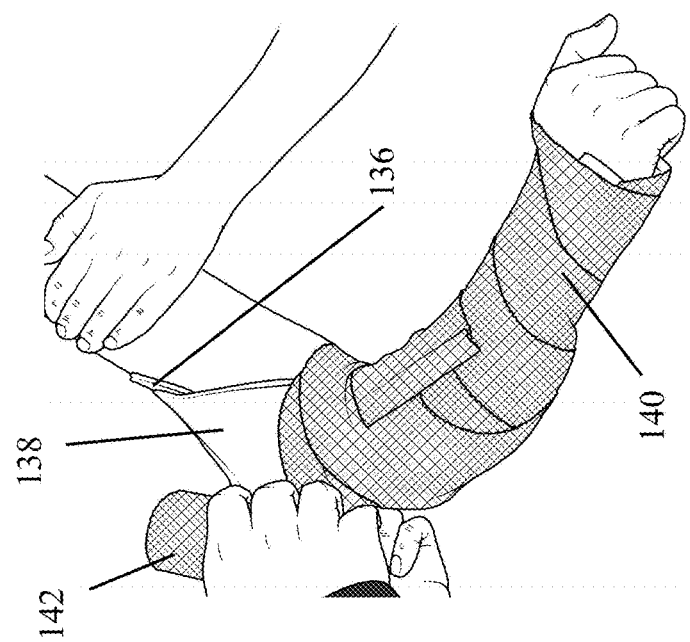
FIG. 31 is an environmental view thereof.
Figure 30:
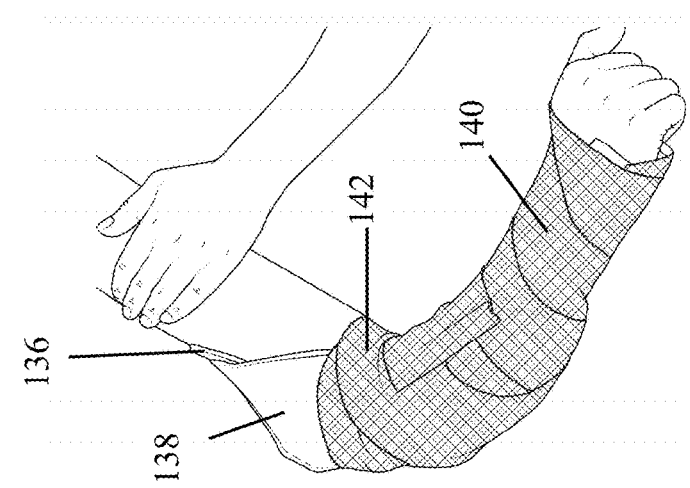
FIG. 30 is an environmental view thereof.
Figure 36:
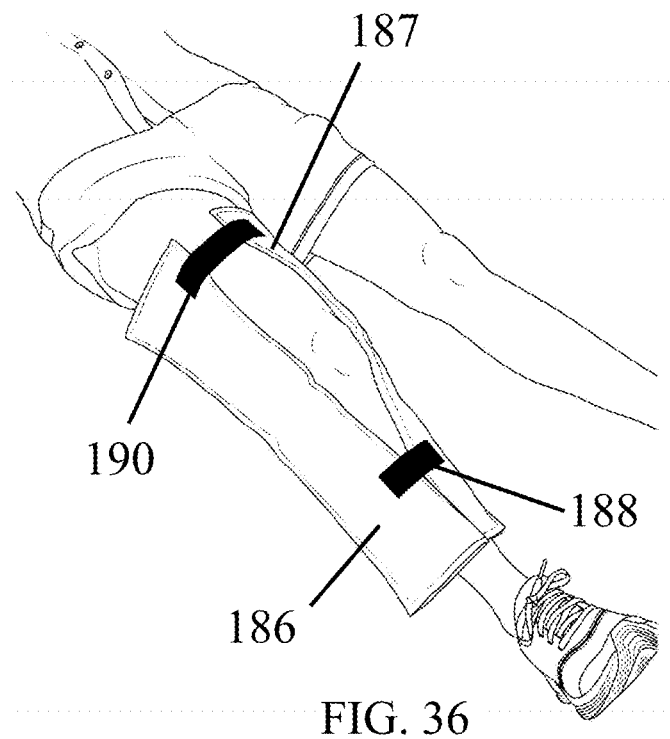
FIG. 36 is an environmental view of one embodiment of the present invention.
Figure 37:
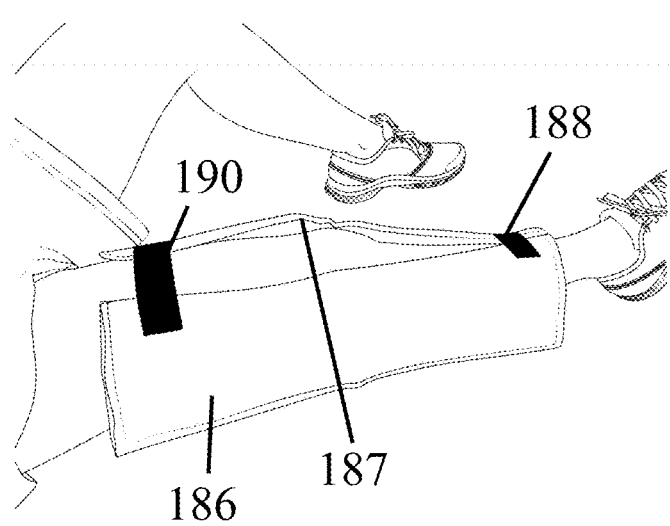
FIG. 37 is an environmental view thereof.
Figure 38:
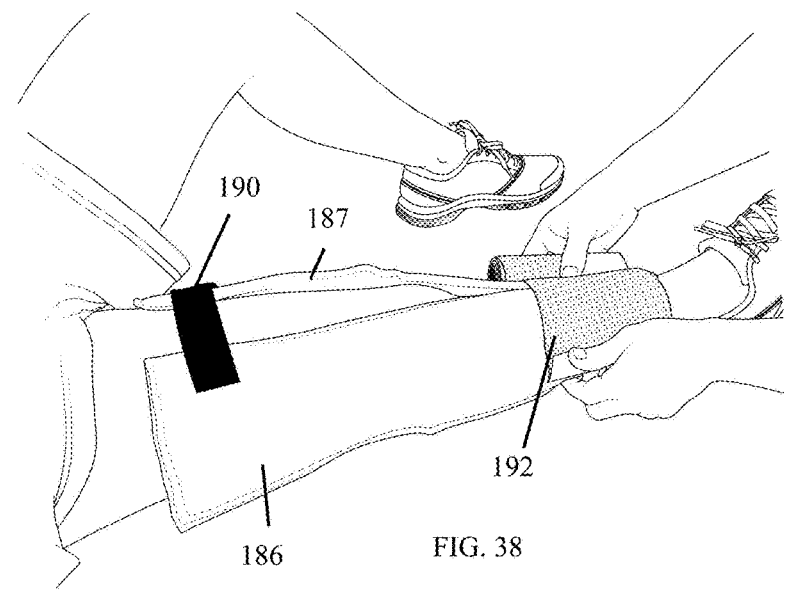
FIG. 38 is an environmental view thereof.
Figure 39:
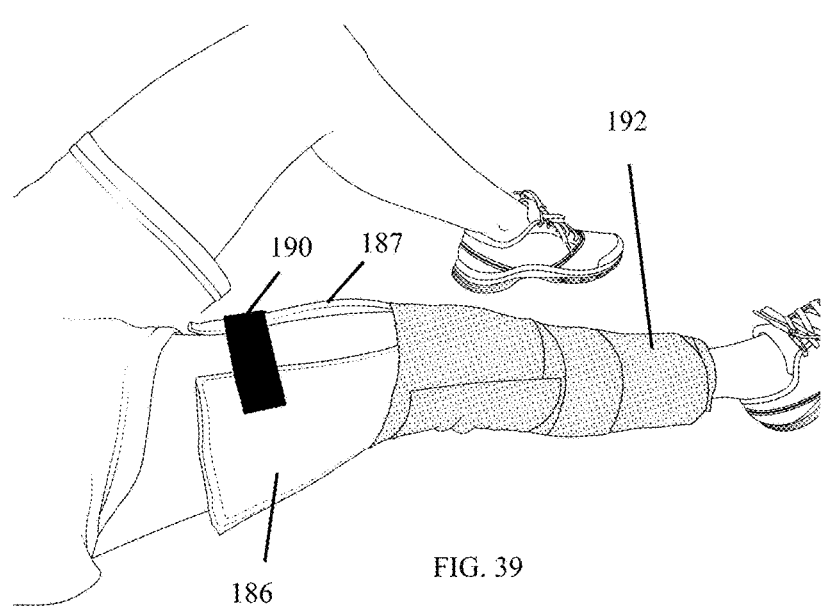
FIG. 39 is an environmental view thereof.
Figure 40:
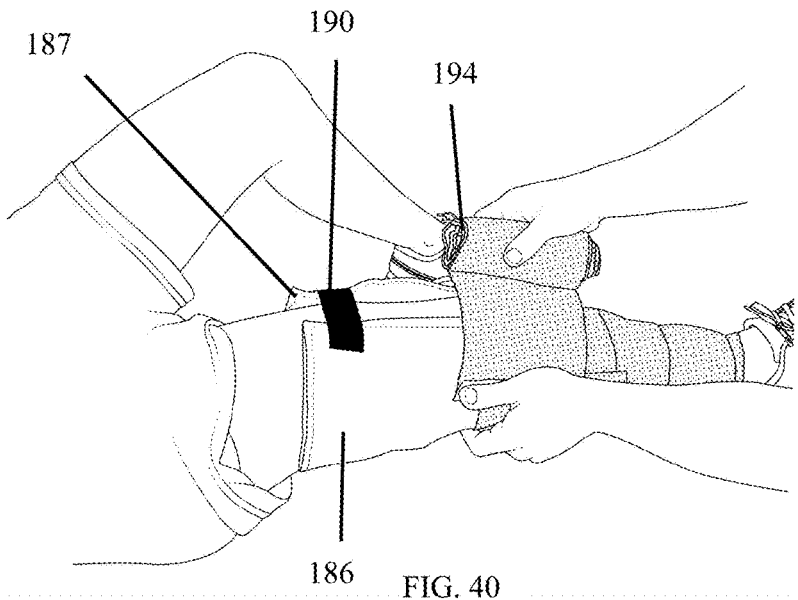
FIG. 40 is an environmental view thereof.
Figure 41:
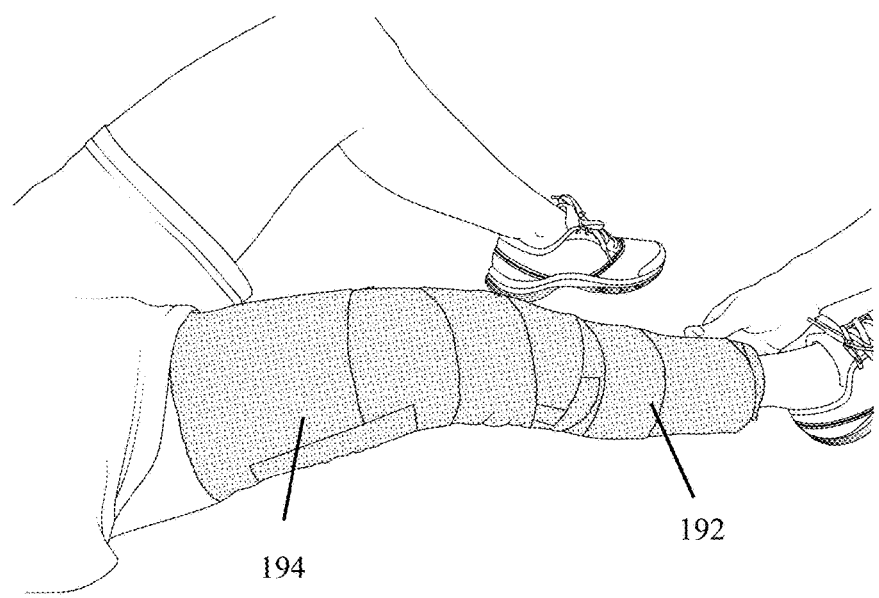
FIG. 41 is an environmental view thereof.
Figure 43:
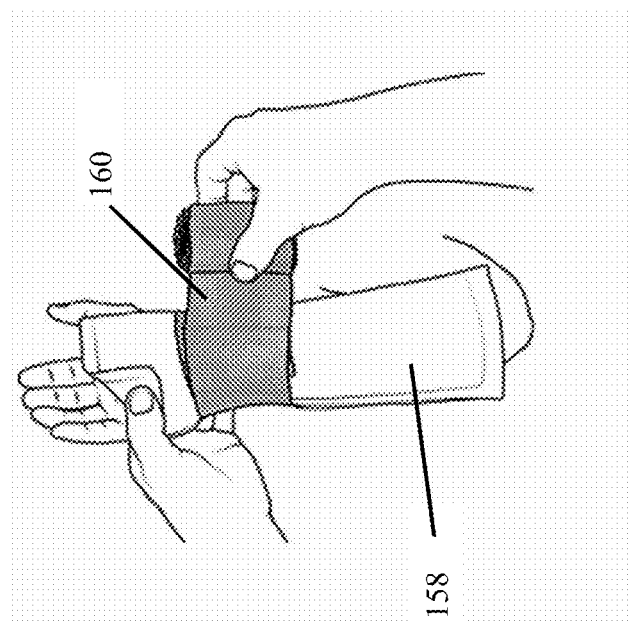
FIG. 43 is an environmental view thereof.

FIG. 20 shows the bandage 106 that is applied to the splint to secure the splint to the user. In one embodiment, the bandage is packaged within a wrapper. The user removes the wrapper from the bandage by twisting the wrapper. The bandage 106 of one embodiment has elastic qualities that enable the bandage 106 to secure the splint to the user. The bandage 106 is wrapped around the user and the splint to secure the splint and stabilize the body part. The bandage 106 is supplied in an appropriate length and width per application to secure the splint to the user. Therefore, the user is not required to size the bandage 106 for each application. The caregiver applies bandage 106 to secure the splint to the user. The applied splint then stabilizes the rigid splint to the injured body part providing stability, circumferential compression, reducing edema, and limiting pain and further injury.

FIGS. 21-26 show the splints 130, 132 and bandages 133, 134 available in an ankle splint kit. The ankle splint kit provides a first splint 130 and a second splint 132. The ankle splint kit also provides a first bandage 133 and a second bandage 134. The ankle splint kit is available in both a child size and an adult size.

The splints 130, 132 of the child size ankle kit ranges from two (2) inches wide to five (5) inches wide, preferably three (3) inches wide. The length of the first splint 130 may range from ten (10) inches to thirty (30) inches, preferably twenty (20) inches. The length of the second splint 132 may range from ten (10) inches to forty (40) inches, preferably twenty six (26) inches. The width of bandages 133, 134 of the child size ankle kit range from two (2) to ten (10) inches in width, preferably four (4) inches.

The splints 130, 132 of the adult size ankle kit range from two (2) inches wide to six (6) inches wide, preferably four (4) inches wide. The length of the first splint 130 may range from ten (10) inches to forty five (45) inches, preferably twenty eight (28) inches. The length of the second splint 132 may range from ten (10) inches to fifty (50) inches, preferably thirty two (32) inches. The width of bandages 133, 134 of the adult size ankle kit range from two (2) to twelve (12) inches in width, preferably six (6) inches.

FIGS. 21-26 also show the instructions for applying the ankle splint kit. These instructions may be provided within the housing 101 at instructions 108. FIGS. 21-26 show the placement of the splints 130, 132 on the leg and ankle of the user for setting the splint.

FIGS. 27-32 show the splints 136, 138 and bandages 140, 142 of elbow splint kit. The elbow splint kit provides a first splint 136 and a second splint 138. The elbow splint kit also provides a first bandage 140 and a second bandage 142. The elbow splint kit is available in both a child size and an adult size.

The splints 136, 138 of the child size elbow kit range from two (2) inches wide to five (5) inches wide, preferably three (3) inches wide for splint 136 and two (2) inches wide for splint 138. The length of the first splint 136 may range from ten (10) inches to thirty (30) inches, preferably eighteen (18) inches. The length of the second splint 138 may range from five (5) inches to twenty (20) inches, preferably eight (8) inches. The bandages 140, 142 of the child size elbow kit range from one (1) to eight (8) inches in width, preferably three (3) inches.

The splints 136, 138 of the adult size elbow kit range from two (2) inches wide to six (6) inches wide, preferably three (3) inches wide. The length of the first splint 136 may range from five (5) inches to thirty (30) inches, preferably twenty two (22) inches. The length of the second splint 138 may range from five (5) inches to twenty (20) inches, preferably ten (10) inches. The bandages 140, 142 of the adult size elbow kit range from two (2) to ten (10) inches in width, preferably four (4) inches.

FIGS. 27-32 also show the instructions for applying the elbow splint kit. These instructions may be provided on the housing 101 at instructions 108. FIGS. 27-32 show the placement of the splints 136, 138 on the arm and elbow of the user for setting the splint.

FIGS. 33-35 show the splint 144 and bandage 146 of forearm splint kit, also called a sugar tong. The forearm splint kit is available in a child size, teen size, and an adult size.

The splint 144 of the child size forearm splint kit ranges from one (1) inch wide to four (4) inches wide, preferably two (2) inches wide. The length of the splint 144 may range from fifteen (15) inches to fifty (50) inches, preferably twenty-six (26) inches. The bandages 146 of the child size forearm splint kit ranges from one (1) to six (6) inches in width, preferably three (3) inches.

The splint 144 of the teen size forearm splint kit ranges from one and a half (1.5) inches wide to five (5) inches wide, preferably three (3) inches wide. The length of the splint 144 may range from fifteen (15) inches to fifty (50) inches, preferably thirty (30) inches. The bandages 146 of the teen size forearm splint kit ranges from one (1) to eight (8) inches in width, preferably four (4) inches.

The splint 144 of the adult size forearm kit ranges from two (2) inches wide to six (6) inches wide, preferably three (3) inches wide. The length of the splint 144 may range from ten (10) inches to fifty (50) inches, preferably thirty five (35) inches. The bandages 146 of the adult size forearm kit ranges from two (2) to ten (10) inches in width, preferably four (4) inches.

FIGS. 33-35 also show the instructions for applying the forearm splint kit. These instructions may be provided on the housing 101 at instructions 108. FIGS. 33-35 show the placement of the splint 144 on the arm and elbow of the user for setting the splint.

FIGS. 36-41 show the splints 186, 187 and bandages 192, 194 of knee splint kit. The knee splint kit provides a first splint 186 and a second splint 187 in a single splint housing such as housing 102. The knee splint kit also provides a first bandage 192 and a second bandage 194. The knee splint kit is available in both a child size and an adult size.

The knee splint kit also provides two fasteners 188, 190. These fasteners attach to each splint 186, 187 to secure the splints together for properly positioning the splints 186, 187 in relation to the user. The fasteners 188, 190 may be an adhesive substance such as tape or a hook and loop fastener, such as Velcro. The fasteners 188, 190 secure the two splints 186, 187 to one another to assist the user in setting the splints. The fasteners enable the user to rest the fasteners over the user's leg to properly position the splints 186, 187. The user may then apply the bandages as shown in FIGS. 36-41.

In one embodiment, the fasteners 188, 190 may be located at or near the top and the bottom of the splints 186, 187. The fasteners 188, 190 may be adjusted on the splint for positioning the splints 186, 187. In one embodiment, the fasteners 188, 190 may be completely removed from each splint 186, 187. Such an embodiment enables the hook and loop fasteners to directly attach to the felt material that encases the fiberglass. The splints 186, 187 of one embodiment are packaged within one splint housing with the fasteners 188, 190 attached as shown in FIGS. 36-41.

The splints 186, 187 of the child size knee kit range from two (2) inches wide to eight (8) inches wide, preferably four (4) inches wide. The length of the splints 186, 187 may range from ten (10) inches to thirty (30) inches, preferably fourteen (14) inches. The bandages 192, 194 of the child size knee kit range from two (2) to ten (10) inches in width, preferably four (4) inches.

The splints 186, 187 of the adult size knee kit ranges from two (2) inches wide to ten (10) inches wide, preferably five (5) inches wide. The length of the splints 186, 187 may range from ten (10) inches to forty (40) inches, preferably eighteen (18) inches. The bandages 192, 194 of the adult size knee kit range from two (2) to twelve (12) inches in width, preferably six (6) inches.

FIGS. 36-41 also show the instructions for applying the knee splint kit. These instructions may be provided on the housing 101 at instructions 108. FIGS. 36-41 show the placement of the splints 186, 187 on the leg of the user for setting the splint.

FIGS. 42-53 show the splint 158 and bandage 160 of wrist/thumb splint kit. The wrist/thumb splint kit is available in both a child size and an adult size.

The splint 158 of the child size wrist splint kit ranges from one half (½) inch wide to six (6) inches wide, preferably two (2) inches wide. The length of the splint 158 may range from five (5) inches to fifteen (15) inches, preferably eight (8) inches. The bandage 160 of the child size wrist splint kit range from one (1) to eight (8) inches in width, preferably two (2) inches.

The splint 158 of the adult size wrist splint kit ranges from one half (½) inch wide to six (6) inches wide, preferably three (3) inches wide. The length of the splint 158 may range from five (5) inches to twenty (20) inches, preferably ten (10) inches. The bandage 160 of the adult size wrist splint kit range from one (1) to eight (8) inches in width, preferably three (3) inches.

Figure 42:
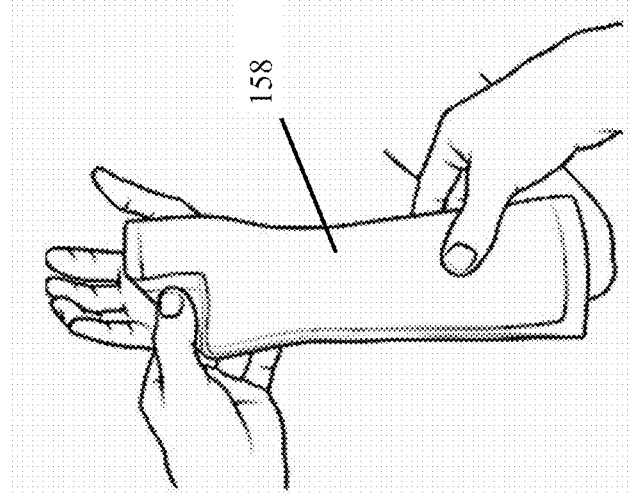
FIG. 42 is an environmental view of one embodiment of the present invention.
Figure 47:
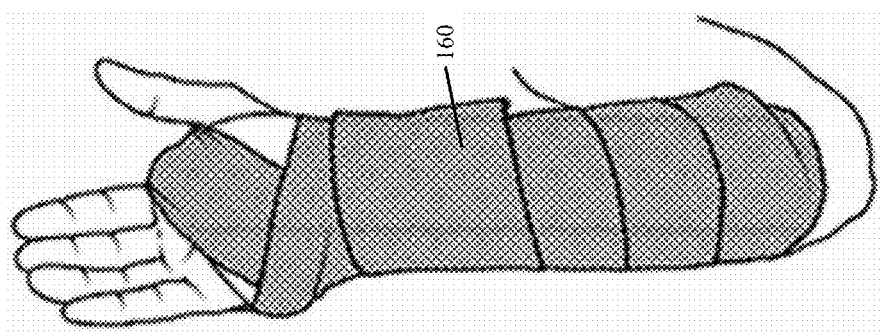
FIG. 47 is an environmental view thereof.
Figure 46:
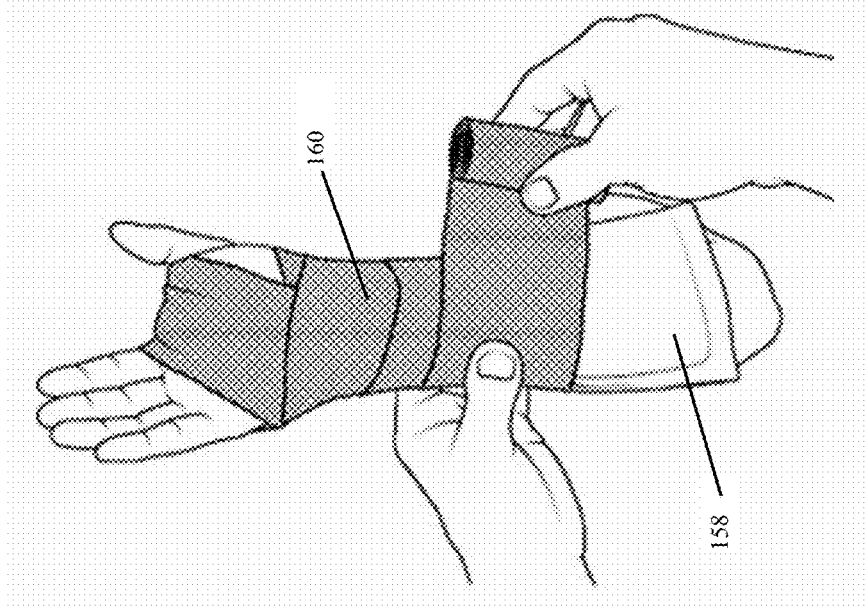
FIG. 46 is an environmental view thereof.
Figure 49:
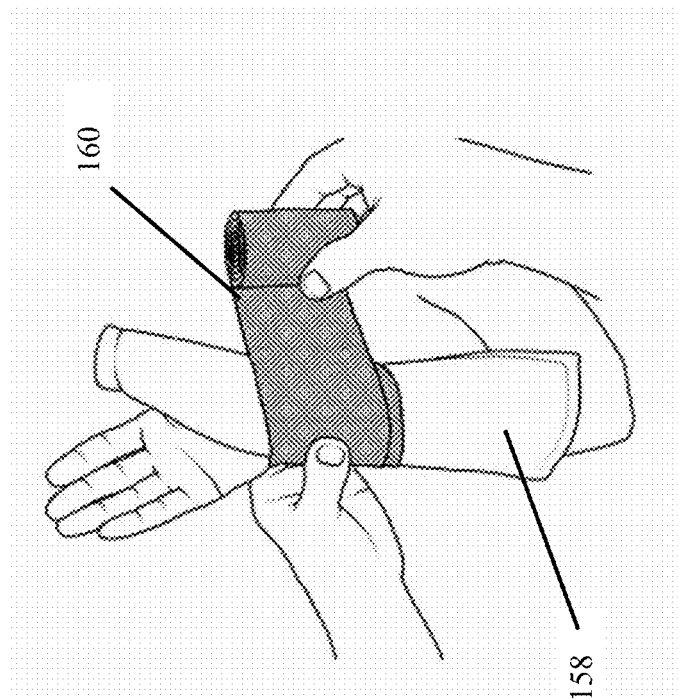
FIG. 49 is an environmental view thereof.

FIGS. 42-47 show the instructions for applying the wrist/thumb splint kit to the wrist. These instructions may be provided on the housing 101 at instructions 108. FIGS. 42-47 show the placement of the splint 158 on the arm and wrist of the user for setting the splint. FIGS. 42-47 also show the application of bandage 160 around splint 158. FIG. 42 shows the adjustment of splint 158 for the user's wrist wherein a portion of the splint 158 is folded outward towards the user's palm.

Figure 48:
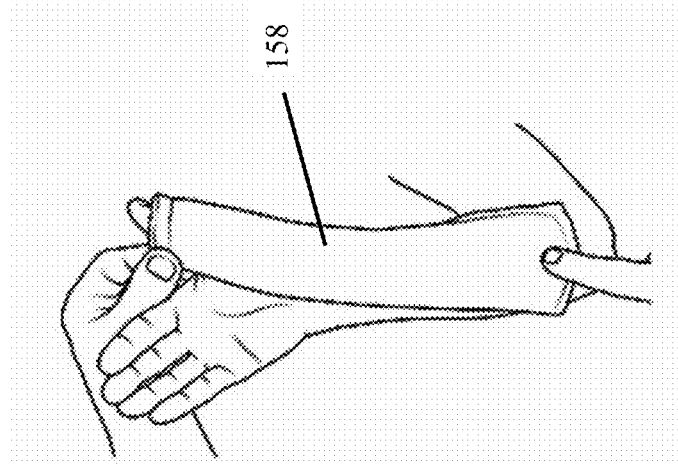
FIG. 48 is an environmental view thereof.

FIGS. 48-53 show the instructions for applying the wrist/thumb splint kit to the thumb. These instructions may be provided on the housing 101 at instructions 108. FIGS. 48-53 show the placement of the splint 158 on the arm and around the thumb of the user for setting the splint. FIGS. 48-53 also show the application of bandage 160 around splint 158. FIG. 48 shows the placement of splint 158 around the user's thumb for stabilizing the thumb.

In one embodiment, such as a kit for use in the doctor's office or other locations, such as the home, where a clean water source is available, the present invention may be packaged without a water source. The kits designed for field use may include the water source. The amount of water provided with each kit may vary depending on the size and type of kit. For example, the kits for field use may provide water containers storing water in the amount equal to or greater than three (3) ounces for both the child and adult wrist and the child forearm. The kits for adult forearm, child elbow, child knee, adult knee, child ankle, and adult ankle may provide water containers storing equal to or greater than six (6) ounces of water. In one embodiment, each kit provides a water container storing 3.4 ounces. The kit may also provide a set of scissors for any sizing that the user or caregiver may choose to make.

In one embodiment, the size of the splints and bandages may vary depending on the type of splint and the use of the splint. The splint kits may provide kits directed towards home use, field use, and professional use. These kits may be directed towards adults, teens, and children. The adult kits, with or without water, may provide splints and bandages of the following

| Boxer: | Splint 4" × 12" | Elastic Bandage 3" wide roll |
|---|---|---|
| Forearm: | Splint 3" × 35" | Elastic Bandage 4" wide roll |
| Ankle: | Splints 4" × 28", 4" × 32" | 2 × Elastic Bandage 6" wide roll |
| Elbow: | Splints 3" × 22", 3" × 10" | 2 × Elastic Bandage 4" wide roll |
| Knee: | 2 × Splints 5" × 18" | 2 × Elastic Bandage 6" wide roll |
| Wrist/Thumb: | Splint 3" × 10" | Elastic Bandage 3" wide roll |

The child kits, with or without water, may provide splints and bandages of the following dimensions:

| Boxer: | Splint 3" × 10" | Elastic Bandage 2" wide roll |
|---|---|---|
| Forearm: | Splint 2" × 26" | Elastic Bandage 3" wide roll |
| Ankle: | Splints 3" × 20", 3" × 26" | 2 × Elastic Bandage 4" wide roll |
| Elbow: | Splints 3" × 18", 2" × 8" | 2 × Elastic Bandage 3" wide roll |
| Knee: | 2 × Splints 4" × 14" | 2 × Elastic Bandage 4" wide roll |
| Wrist/Thumb: | Splint 2" × 8" | Elastic Bandage 2" wide roll |

Figure 54:
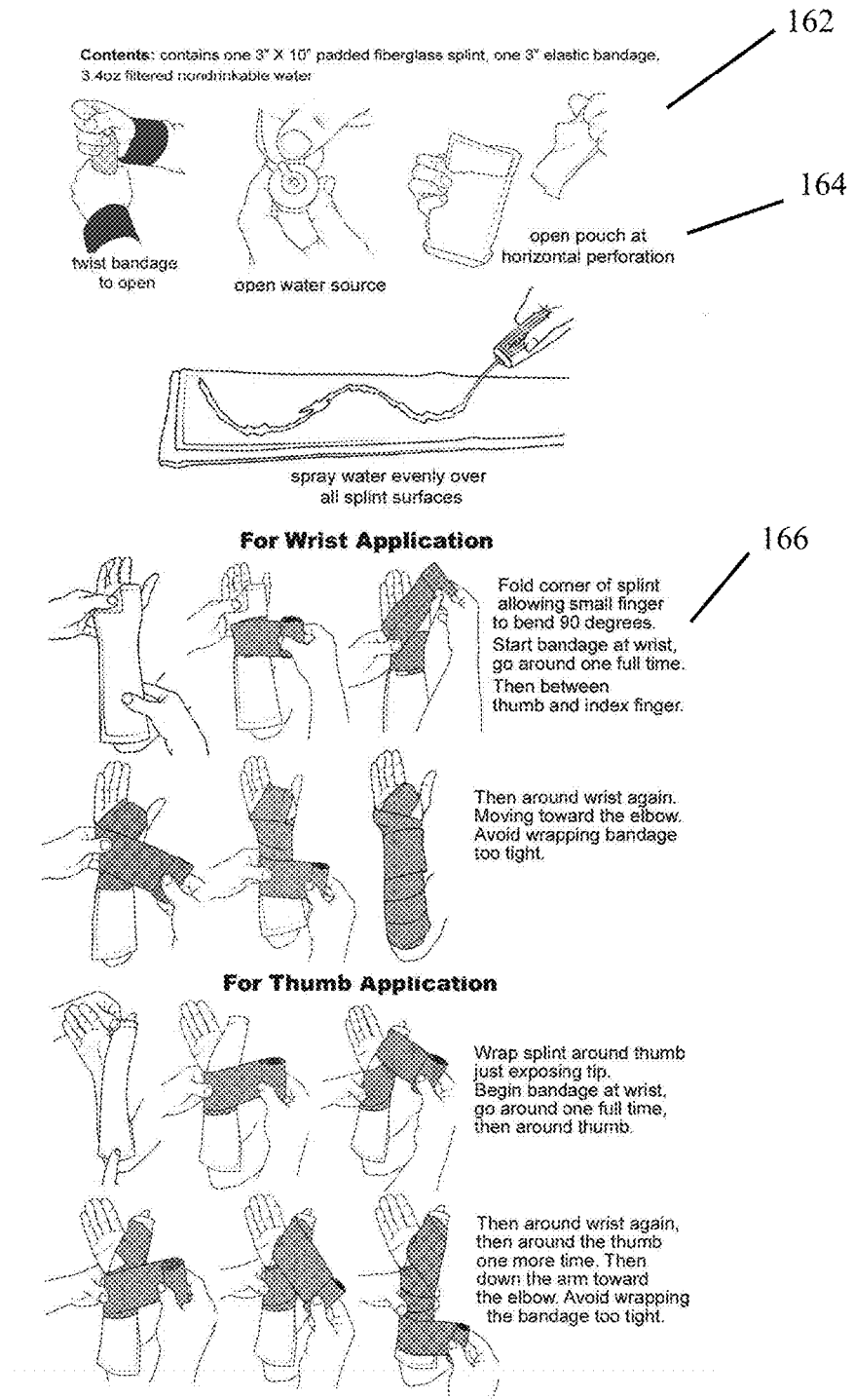
FIG. 54 is a front view of instructions of one embodiment of the present invention.

The teen sized splints will be available between the sizes for the adults and the children. FIGS. 54-60 show the instructions of different embodiments of the present invention. The instructions demonstrate the method of applying water to the splint to activate the splint. The instructions demonstrate activating the splint with a water source packaged with the splint kit as shown in FIG. 54 and activating the splint with a faucet as shown in FIG. 55.

FIGS. 54 and 55 show the wrist/thumb splint instructions with water source 162 and the wrist/splint instructions without water source 168. Instructions 162 show a method 164 of activating the splint with a water source stored within the kit. Instructions 168 show a method 170 of activating the split with water from the faucet.

FIGS. 54 and 55 also show method 166 of applying the splint to the user. Method 166 shows the application of the splint and bandage to the user's wrist or thumb according to the injury to be stabilized.

Figure 56:
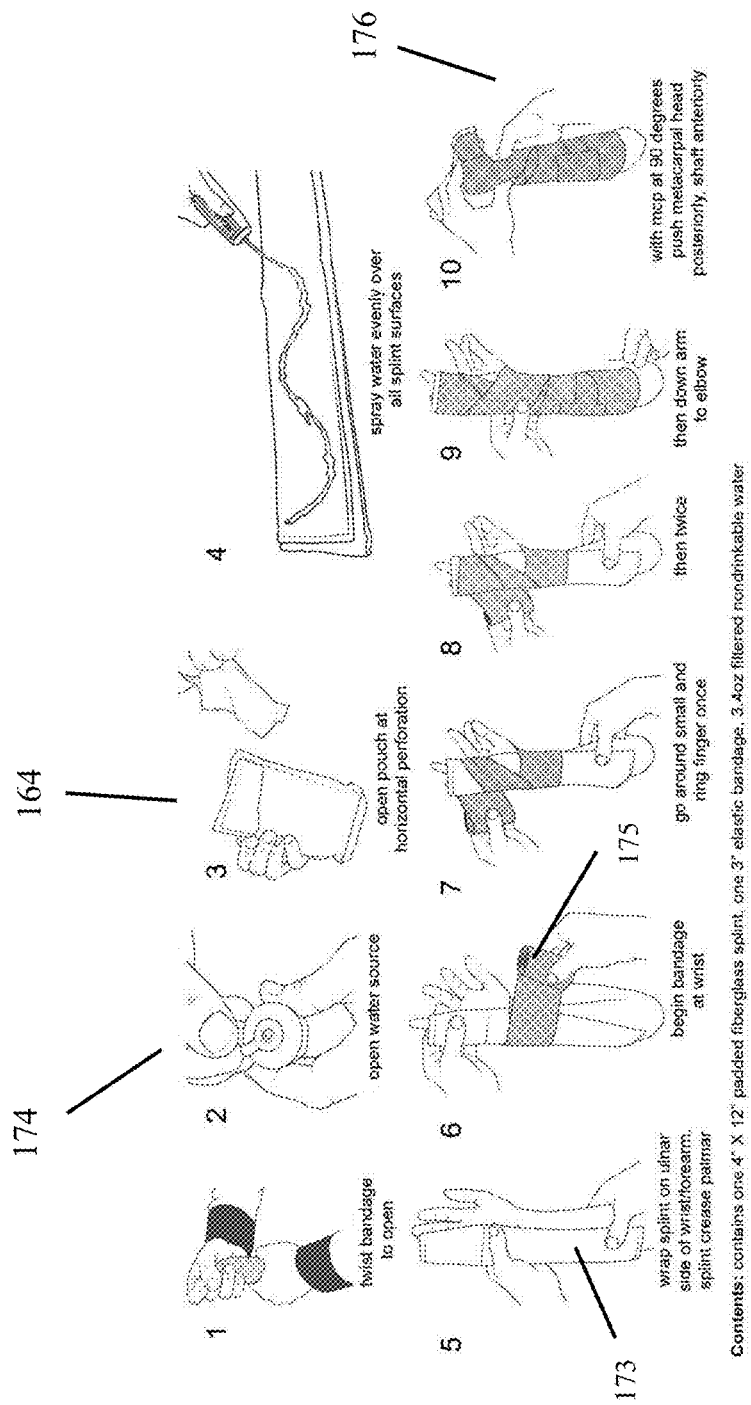
FIG. 56 is a front view of instructions of one embodiment of the present invention.

FIG. 56 shows the boxer instructions 174 with the method 164 of activating the splint. Instructions 174 also show method 176 of applying the splint 173 and bandage 177 for stabilizing a boxer injury. These boxer instructions 174 demonstrate the method for applying the boxer splint kit. These instructions 174 may be provided on the housing 101 at instructions 108. These instruction 174 show the placement of the splint 173 on the wrist and hand of the user for setting the splint.

FIG. 56A shows the splint 173 of a boxer splint kit. The boxer splint kit is available in both a child size and an adult size.

The splint 173 of the child size boxer splint kit ranges from one (1) inch wide to five (5) inches wide, preferably three (3) inches wide. The length of the splint 173 may range from five (5) inches to fifteen (15) inches, preferably ten (10) inches. Boxer splint 173 provides a notch 177 for manipulating splint 173. The notch 177 of one embodiment fully encases the fiberglass/hardening material to avoid exposed fiberglass. The notch 177 is located two inches from one side of the splint 173. The notch 177 and extends 1 and ½ inches (1.5 inches) with a width of a quarter inch (¼ inch). The bandage 175 of the child size boxer splint kit ranges from one (1) to six (6) inches in width, preferably three (3) inches.

The splint 713 of the adult size boxer kit ranges from two (2) inches wide to six (6) inches wide, preferably four (4) inches wide. The length of the splint 144 may range from six (6) inches to eighteen (18) inches, preferably twelve (12) inches. Boxer splint 173 provides a notch 177 for manipulating splint 173. The notch 177 of one embodiment fully encases the fiberglass/hardening material to avoid exposed fiberglass. The notch 177 is located two and three quarters inches (2.75 inches) from one side of the splint 173. The notch 177 extends two inches (2 inches) with a width of a quarter inch (¼ inch). The bandage 175 of the adult size boxer kit ranges from one (1) to six (6) inches in width, preferably three (3) inches.

Figure 57:
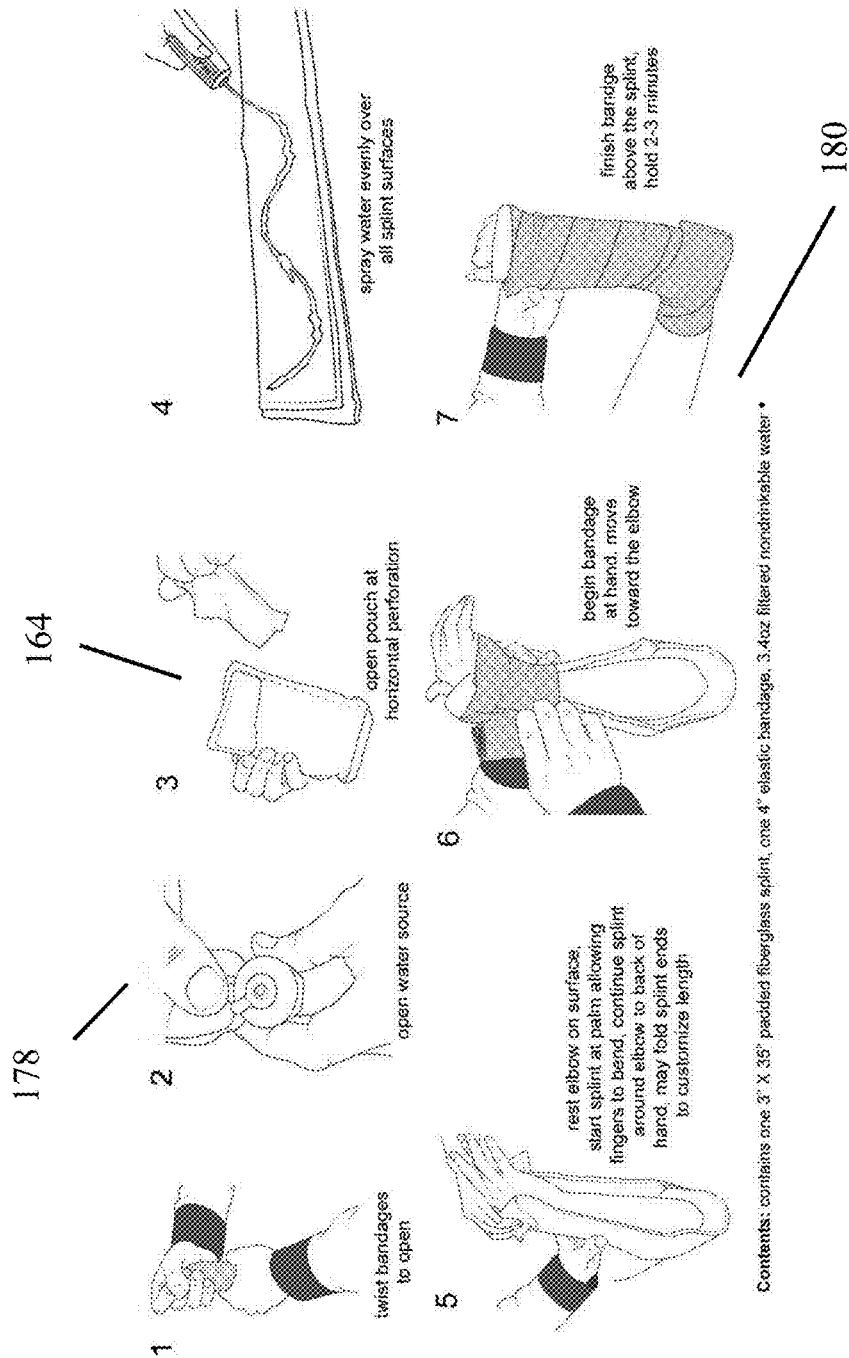
FIG. 57 is a front view of instructions of one embodiment of the present invention.

FIG. 57 shows the forearm instructions 178 with the method 164 of activating the splint. Instructions 178 also show method 180 of applying the splint and bandage to stabilize the forearm.

Figure 58:
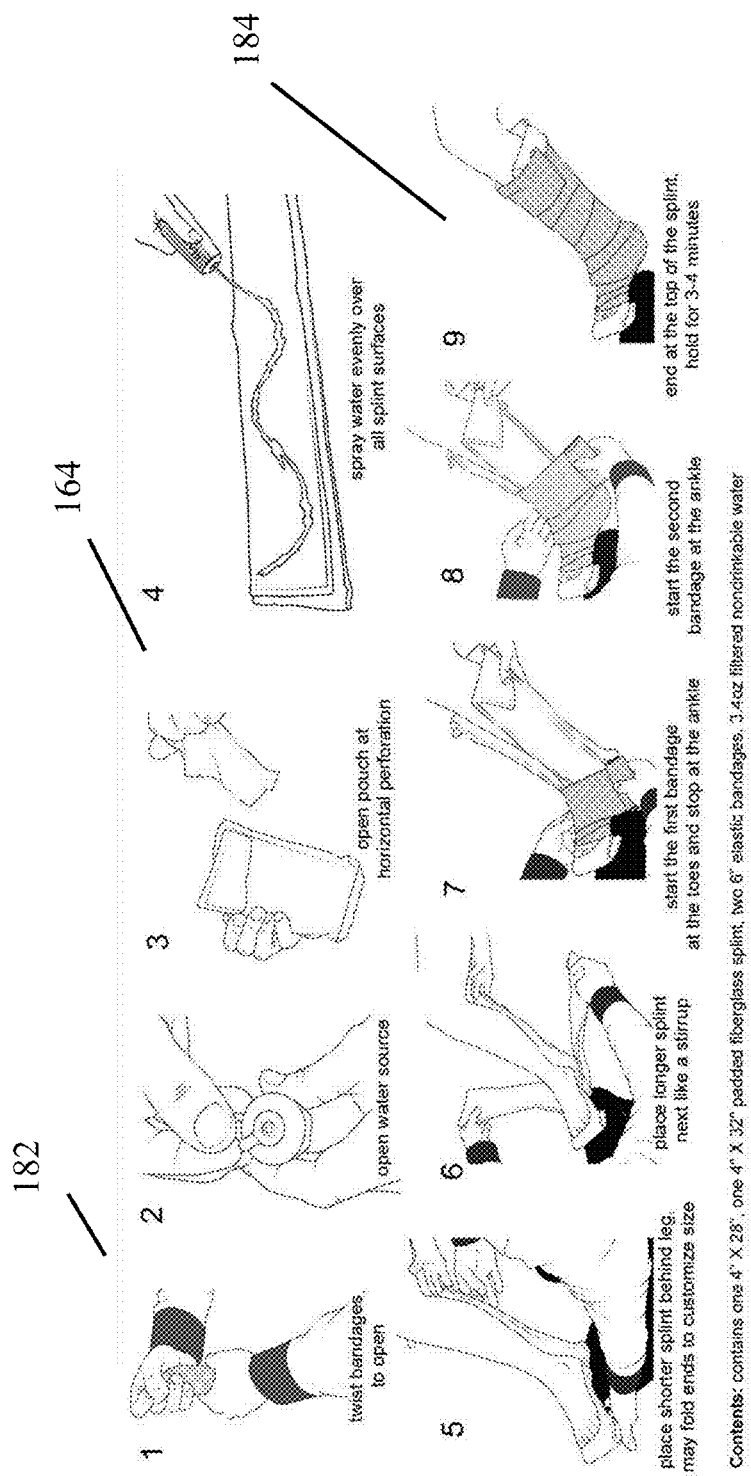
FIG. 58 is a front view of instructions of one embodiment of the present invention.

FIG. 58 shows the ankle instructions 182 with the method 164 of activating the splint. Instructions 182 also show method 184 of applying the splint and bandage to stabilize the ankle.

Figure 59:
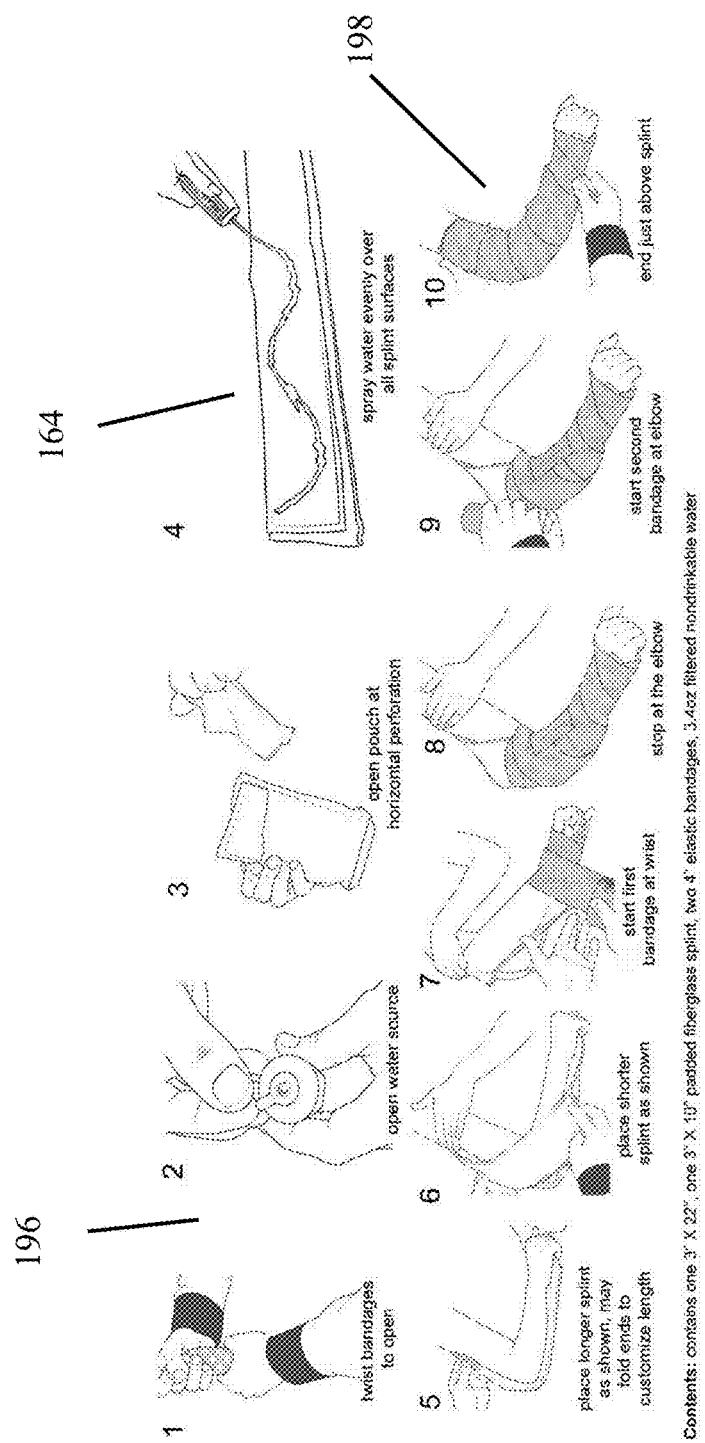
FIG. 59 is a front view of instructions of one embodiment of the present invention.

FIG. 59 shows the elbow instructions 196 with the method 164 of activating the splint. Instructions 196 also show method 198 of applying the splint and bandage to stabilize the elbow.

Figure 60:
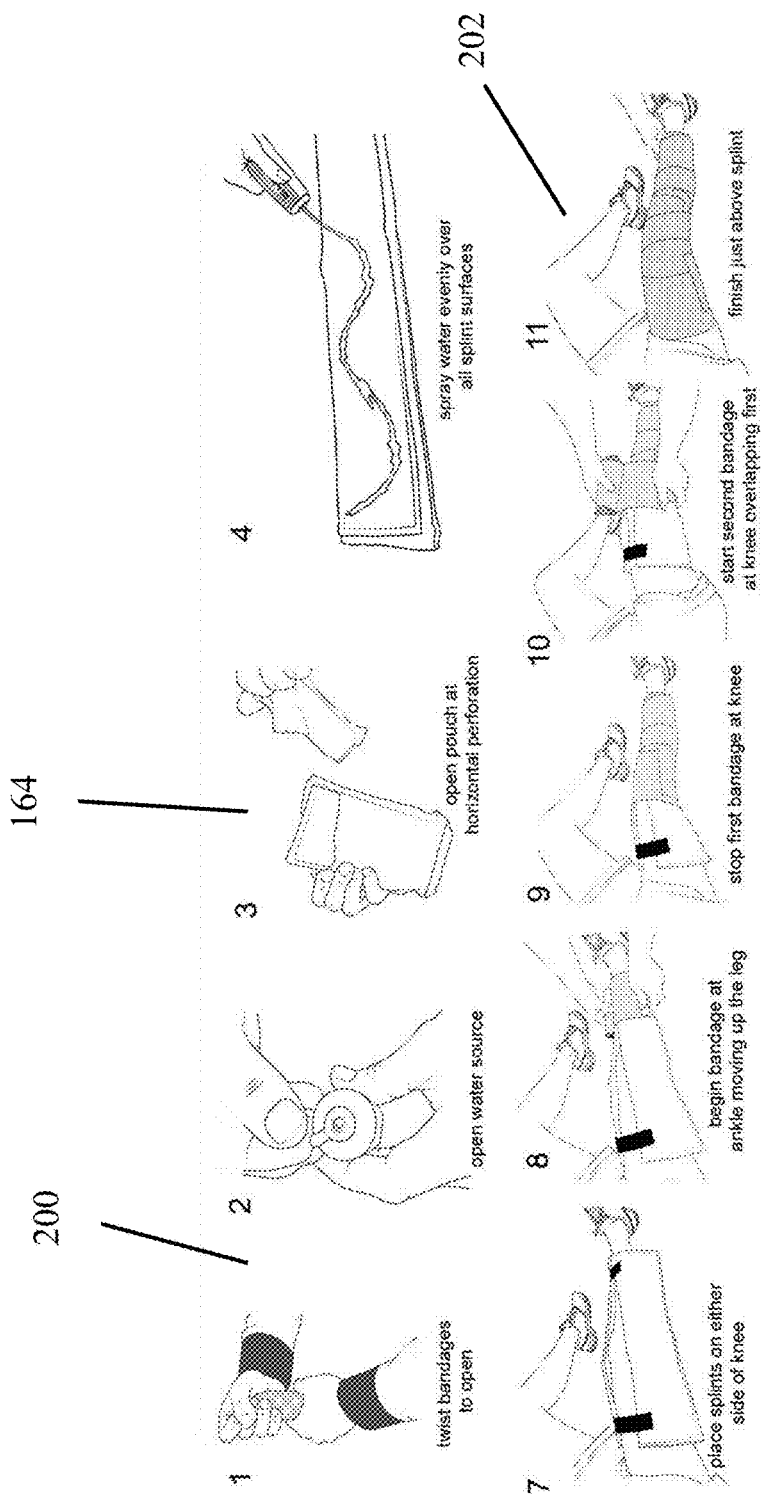
FIG. 60 is a front view of instructions of one embodiment of the present invention.

FIG. 60 shows the knee instructions 200 with the method 164 of activating the splint. Instructions 190 also show method 202 of applying the splint and bandage to stabilize the knee.

FIGS. 56-60 show instructions for activating the different splints with a water source packaged within the kit. The instructions shown in FIG. 56-60 may be modified to show the method 170 of activating the different splints without a water source packaged within the kit as shown in FIG. 55.

Figure 61:
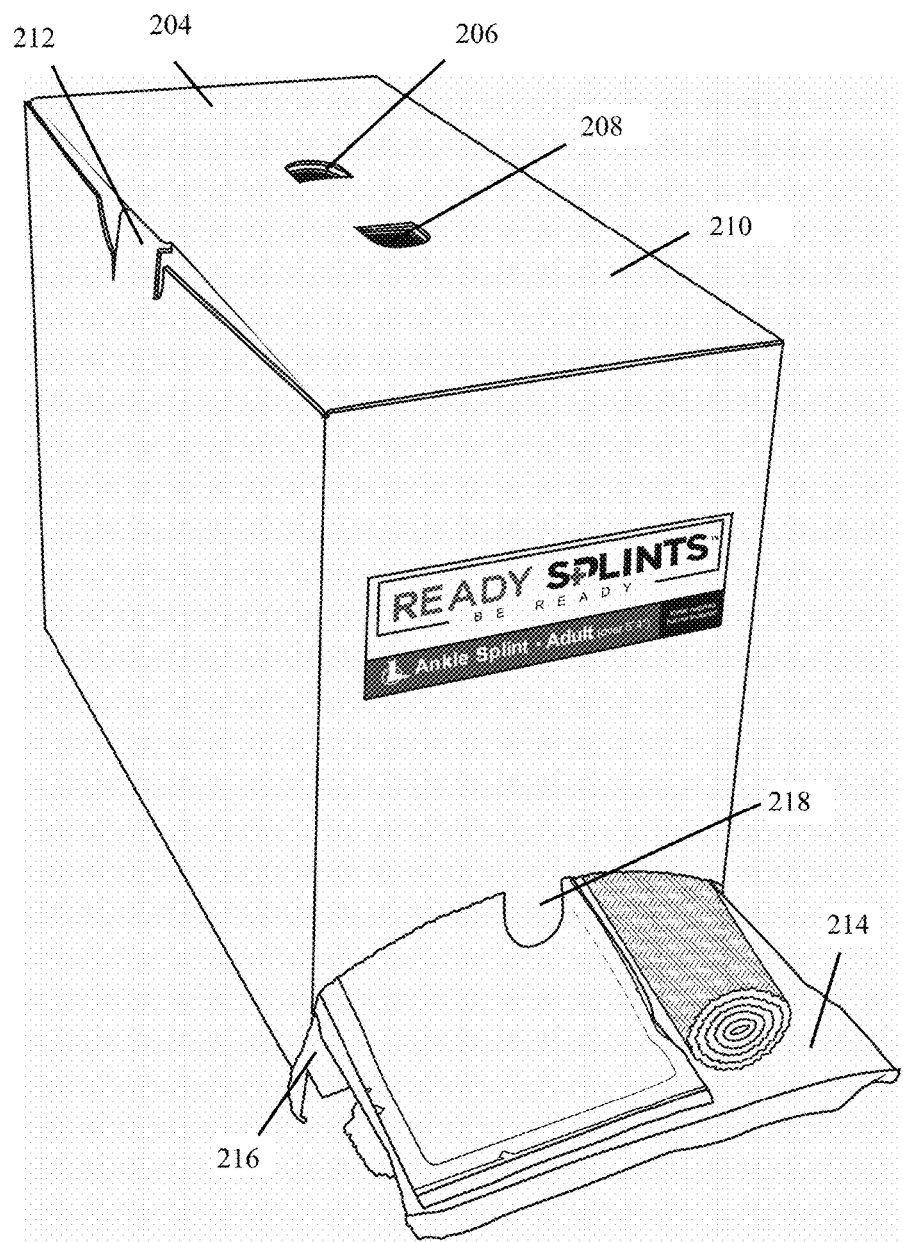
FIG. 61 is an environmental view of one embodiment of the present invention.

FIG. 61 shows container 204 for storing multiple splint kits 214. In one embodiment, container 204 stores splint kits designed for a specific body part of a specific size. The caregiver removes the splint kits 214 from the container 204 through aperture 216. In one embodiment, container 204 is perforated at aperture 216 to simplify the process of opening the container 204. The user presses opening finger 218 inwards and pull the flap outward to gain access into container 204.

The user may also reload container 204 with splints. The user opens tab 212 and lifts open top 210. Tab 212 secures the top 210 in the closed positioning by placing the tab 212 into an aperture of top 210. The user inserts his/her fingers into apertures 206, 208 located on top 210 and pulls upwards to open top 210. The user can then access the contents of container 204 through top 210. The user can remove kits 214 from container 204. The user can also refill container 204 with additional kits 214.

The splint kit of the present invention has been described as being applied to a human being. Splints kits may also be developed for pets and other animals. The number and size of splints and bandages will vary according to the size of the animal and the injury to be treated.

An antimicrobial and/or antibacterial coating may also be applied to the splint to reduce bacteria growth within the splint. The antimicrobial and/or antibacterial coating also reduces odors from forming in the splint.

A hydrophilic coating may also be applied to the splint. The hydrophilic coating attracts water for wetting the splint to activate the splint.

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A kit for splinting at least one body part of a user, the kit comprising:
   a first splint constructed from a hardening material that hardens when wetted, the first splint sized for a specific body part and size of the user wherein the hardening material of the first splint is fully encased;
   a splint housing providing a moisture proof seal around the first splint wherein the first splint is stored within the splint housing;
   a first opening notch of the splint housing formed on a first side of the splint housing near a first end of the splint housing, wherein the first opening notch enables removal of at least a portion of the splint housing to create a first opening in the splint housing wherein the splint housing limits removal of the first splint through the first opening;
   a second opening notch of the splint housing formed on the first side of the splint housing, the first opening notch located between the second opening notch and the first end of the housing along the first side of the splint housing wherein the second opening notch remains on the splint housing after removal of the portion of the splint housing, the second opening notch enabling removal of an additional portion of the splint housing to enlarge the first opening to enable passage of the first splint through the first opening;
   wherein the first opening notch extends inward at an angle towards a second side of the housing located adjacent the first side of the splint housing;
   wherein the second opening notch extends inward towards a third side of the housing located opposite the first side of the housing;
   a third opening notch located on the second side of the splint housing wherein the first opening notch and third opening notch are configured to create a first opening by removing a portion of the splint housing between the first opening notch and the third opening notch wherein the first opening notch is angled towards the third opening notch to align the first opening notch with the third opening notch; and
   a fourth opening notch located on the third side of the splint housing wherein the second opening notch and fourth opening notch are configured to enlarge the first opening, wherein the second opening notch extends inward toward the fourth opening notch to align the second opening notch with the fourth opening notch.

2. The kit of claim 1 wherein the first opening notch and the third opening notch are angled and directed towards each other.

3. The kit of claim 1 wherein the second opening notch and the fourth opening notch are aligned on the splint housing and extend inwards towards each other.

4. A kit for splinting at least one body part of a user, the kit comprising:
   a first splint that hardens when contacted with moisture, wherein the splint is sized for a single use application;
   a splint housing providing a moisture proof seal around the splint wherein the splint is stored within the splint housing;
   a first opening notch formed on a first side of the splint housing wherein the first opening notch enables removal of at least a portion of the splint housing to create a first opening in the splint housing;
   a second opening notch formed on the first side of the splint housing located exterior of the first opening notch, wherein the second opening notch remains on the splint housing after removal of the portion of the splint housing, the second opening notch enabling removal of at least a portion of the splint housing to enlarge the first opening;
   a main housing storing the bandage, the splint housing, and the splint;
   wherein the first opening notch is angled towards a second side of the splint housing wherein the second side of the splint housing abuts against the first side of the splint housing, the first opening notch angling towards the second side from an outer edge of the first side of the splint housing towards the second side of the splint housing;
   the second opening notch is directed laterally inwards towards a third side of the splint housing located opposite of the first side of the splint housing;
   a third opening notch located on a side opposite of the first side of the splint housing; and
   a fourth opening notch located on the second side of the splint housing that abuts against the first side of the splint housing.

5. The kit of claim 4 further comprising:
   a second splint constructed from fiberglass that hardens when contacted with moisture, wherein the second splint is sized for a single use application, the second splint being sized based upon the body part to be splinted and the size of the user; and
   wherein the splint housing stores both the first splint and the second splint.

* * * * *